(12) United States Patent
Donald et al.

(10) Patent No.: US 6,212,956 B1
(45) Date of Patent: Apr. 10, 2001

(54) HIGH OUTPUT CAPACITATIVE GAS/LIQUID DETECTOR

(75) Inventors: David K. Donald, Mountain View; Leslie A. Field; Phillip W. Barth, both of Portola Valley; Storrs T. Hoen, Brisbane, all of CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/221,636

(22) Filed: Dec. 23, 1998

(51) Int. Cl.$^7$ .................................................. G01L 9/12
(52) U.S. Cl. ............................................................ 73/724
(58) Field of Search ...................... 73/718, 724; 257/298, 257/300, 301, 303, 306, 307, 308; 361/277, 281, 282, 283.1–283.4, 284, 287

(56) References Cited

U.S. PATENT DOCUMENTS

| 4,084,101 | * | 4/1978 | Sher ...................................... 290/1 R |
| 5,365,783 | | 11/1994 | Zweifel ................................... 73/304 |
| 5,986,301 | * | 11/1999 | Fukushima et al. .................. 257/306 |

OTHER PUBLICATIONS

Adamson, "Physical Chemistry of Surfaces", Chapter V, pp. 169–191. (No Date).

* cited by examiner

*Primary Examiner*—William Oen
(74) *Attorney, Agent, or Firm*—Ian Hardcastle

(57) ABSTRACT

A gas or liquid detector that includes a capacitative sensor and a capacitance detector. The capacitative sensor includes a first electrode and a second electrode separated from one another, and additionally includes Debye elements extant in the liquid adjacent such portions of the electrodes that are in contact with the liquid. The Debye elements each include a Debye capacitor with an associated shunt conductor. The shunt conductor has an exponentially-increasing conductance versus voltage characteristic. The Debye element adjacent the first electrode and the Debye element adjacent the second electrode are connected in series by conduction through the liquid. The Debye element adjacent at least the first electrode has a substantially greater capacitance than the capacitance between the electrodes absent the Debye elements. The capacitance detector is connected to the capacitative sensor and measures the capacitance of the capacitative sensor by applying an alternating voltage between the electrodes. The alternating voltage has a voltage amplitude less than the voltage amplitude at which the Debye element extant adjacent at least the first electrode ceases to be predominantly capacitive. By measuring the capacitance of the capacitative sensor using an alternating voltage having a voltage amplitude less than the voltage amplitude at which the Debye element ceases to be predominantly capacitive, the capacitances measured are one or more orders of magnitude greater than the capacitances conventionally measured between electrodes in contact with a liquid.

23 Claims, 8 Drawing Sheets

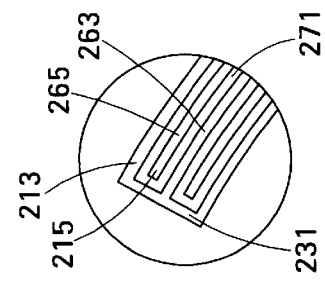
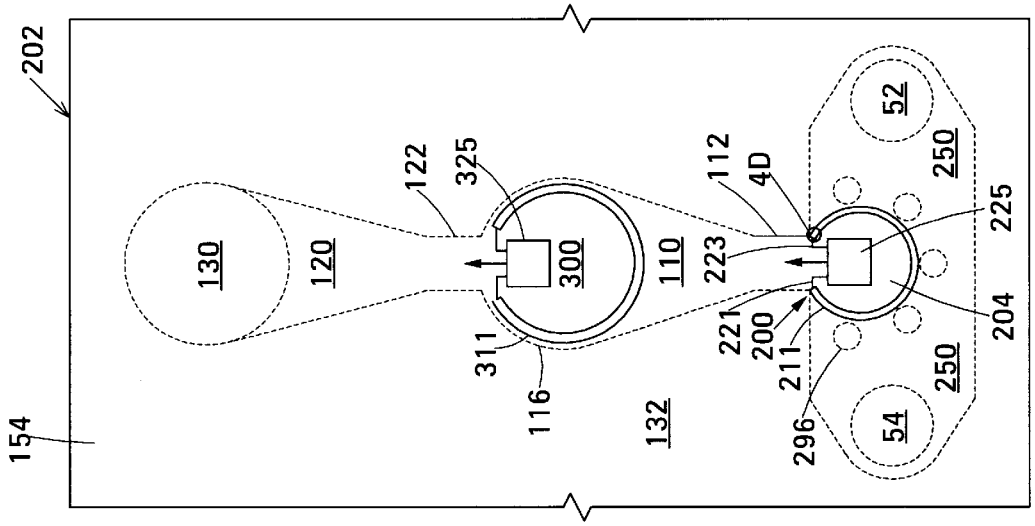
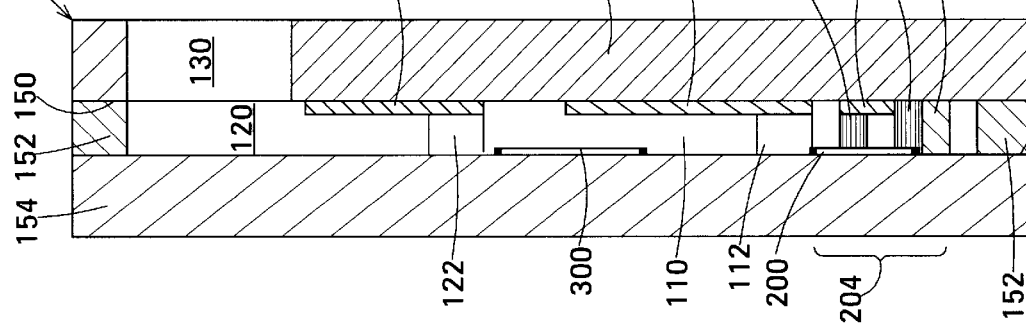
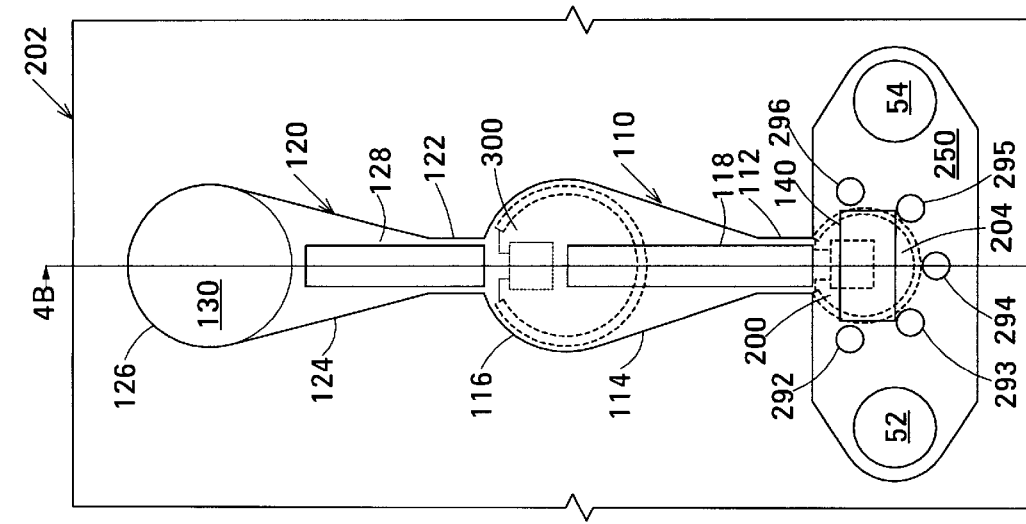

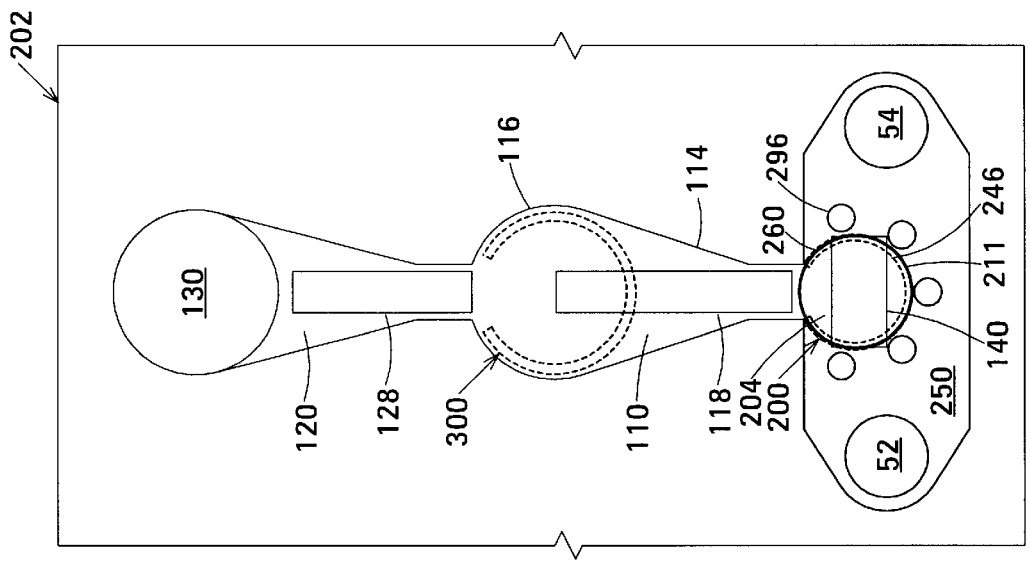
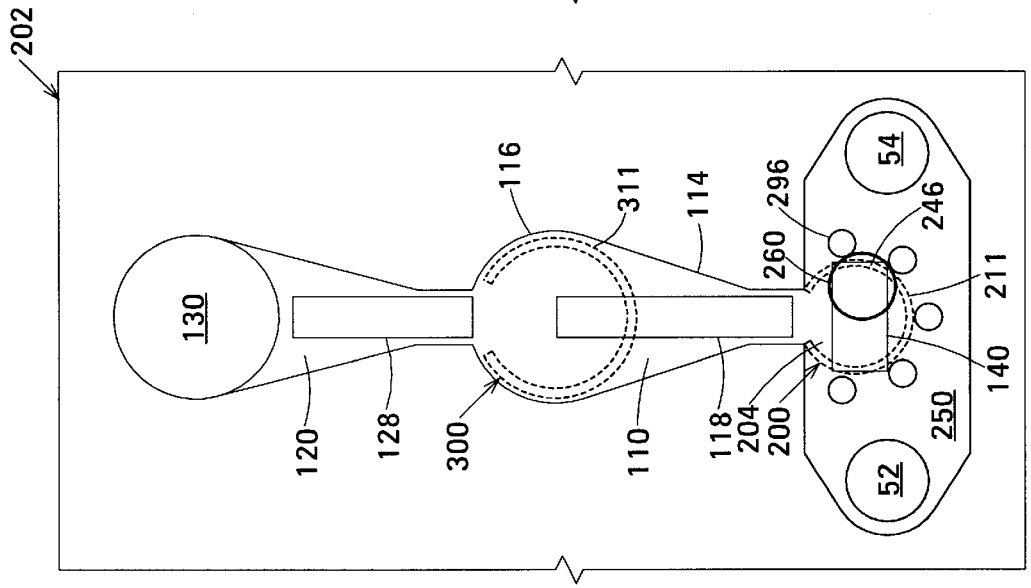
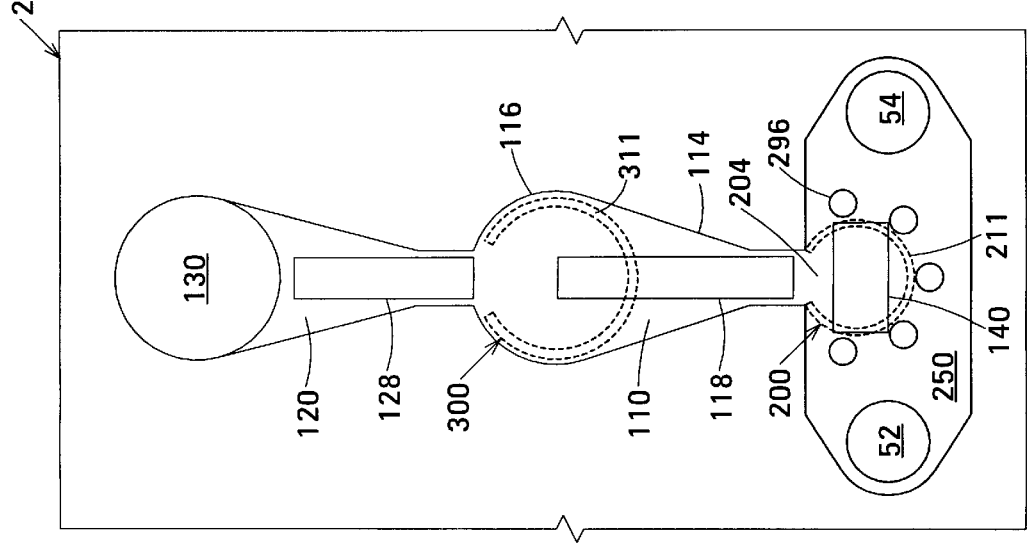

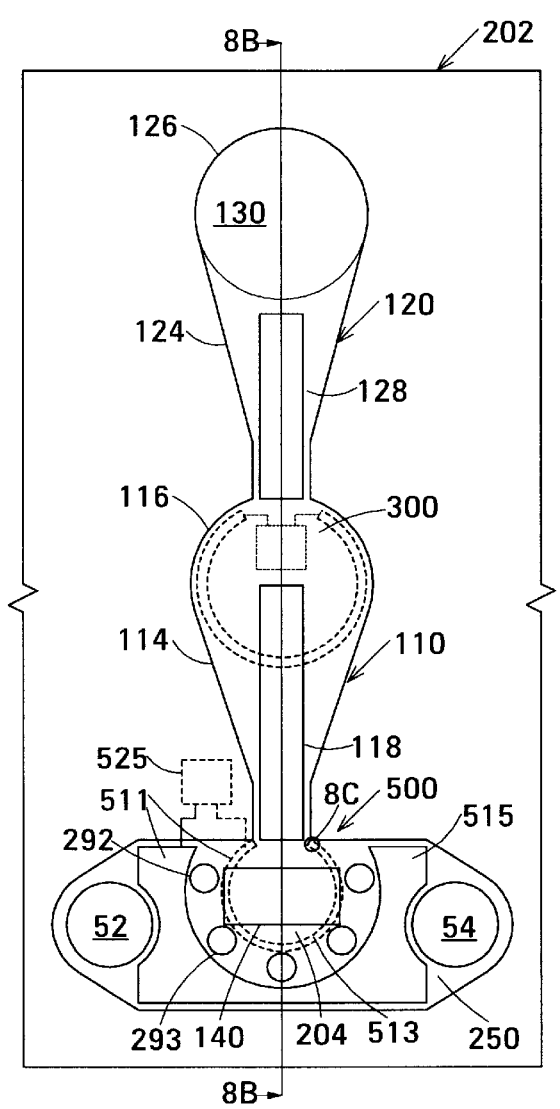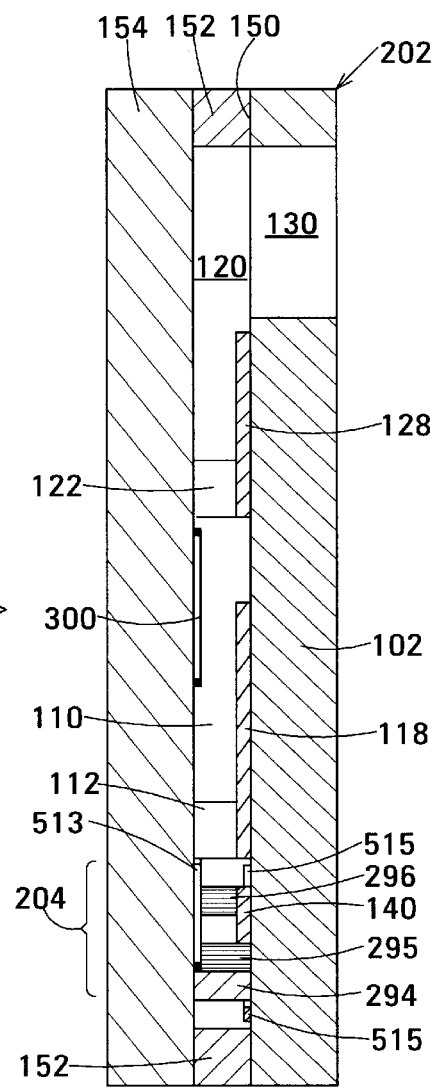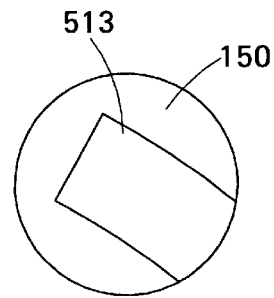
FIG. 8A
FIG. 8B
FIG. 8C

HIGH OUTPUT CAPACITATIVE GAS/LIQUID DETECTOR

FIELD OF THE INVENTION

The invention relates to a detector for detecting the presence or absence of a liquid or the presence or absence of a gas in a microfluidics system, and in particular to a capacitative gas/liquid detector that provides a large change of capacitance per unit area.

BACKGROUND OF THE INVENTION

In microfluidics systems, it in often necessary to detect the presence or absence of a liquid or to detect the presence or absence of a gas at a predetermined location in such systems. For example, U.S. patent application Ser. No. 09/114,978, the entire disclosure of which is incorporated herein by reference, assigned to the assignee of this disclosure, discloses bubble valve-based pressure regulators that operate in response to pressure sensors that use a capacitative detector to detect the level of liquid in a capillary array. U.S. patent application Ser. No. 09/116,427, the entire disclosure of which is incorporated herein by reference, and also assigned to the assignee of this disclosure, discloses pressure regulators that include an active primary pressure regulator and a passive secondary pressure regulator. An array of capillaries is used as the secondary pressure regulator. The primary pressure regulator is controlled by a controller that operates in response to a capacitative pressure sensor coupled to the capillary array. Some embodiments of the capacitative pressure sensor detect the presence or absence of liquid in ones the capillaries constituting the capillary array. Other embodiments detect the liquid level in the capillary array.

In a United States patent application simultaneously filed with this disclosure and entitled Gas Extraction Device for Extracting Gas from a Microfluidics System, the entire disclosure of which is incorporated herein by reference, two of the inventors and others disclose a device for use in a microfluidics system that extracts from the system gas released from the liquid in the system. Some of the embodiments disclosed employ an active control system that operates in response to a detector that detects when a bubble of gas that accumulates at a location in the system has grown to a size that justifies extraction.

Conventional capacitative detectors for detecting the presence of a liquid typically include a pair of opposed conductive plates and a capacitance detector circuit that measures the capacitance between the plates. Interleaved conductive fingers located on one surface may be used instead of the opposed conductive plates, and the term plates will be understood to encompass such interleaved fingers. The capacitance detector circuit applies an alternating signal having an amplitude of several volts between the plates to measure the capacitance. When measured in this way, the capacitance between the conductive plates is proportional to the area of the plates and the dielectric constant of the medium separating the plates, and is inversely proportional to the distance between the plates. Since liquids generally have a greater dielectric constant than gases, the capacitance measured between the plates when the plates are in contact with a liquid is greater than that measured when the plates are in contact with a gas such as air. However, the change in capacitance is relatively small, and can be masked by the stray capacitances between the conductive plates and other elements of the microfluidics system. Consequently, it is often difficult to detect whether the plates are in contact with the liquid or not. This is especially true when a simple, low-cost capacitance detector circuit is used. The detection reliability can be increased by increasing the area of the plates, but restraints imposed by the small dimensions of the locations where the plates are positioned to detect the presence or absence of the liquid often prevent the area of the plates from being increased sufficiently to provide the sought-for detection reliability.

Thus, what is needed is a capacitative gas/liquid detector that can reliably and easily detect a change in capacitance caused by a liquid contacting a sensor. What is also needed is a capacitative gas/liquid detector that can easily be fabricated using the same micromachining techniques used to fabricate the other major elements of the microfluidics system.

SUMMARY OF THE INVENTION

The invention provides a gas or liquid detector, abbreviated below as gas/liquid detector, for an ionic liquid. The detector includes a capacitative sensor and a capacitance detector. The capacitative sensor has a capacitance and includes a pair of electrodes separated from one another. The electrodes are positioned to be capable of contact with the ionic liquid. Contact between one of the electrodes and the ionic liquid forms a Debye element in the ionic liquid. The Debye element includes a capacitative element and an associated shunt conductor. The shunt conductor has an exponentially-increasing conductance-versus-voltage characteristic. The capacitance detector is connected to the capacitative sensor and measures the capacitance of the capacitance sensor by applying an alternating voltage between the electrodes. The alternating voltage has a voltage amplitude less than the voltage amplitude at which the Debye element ceases to be predominantly capacitative.

The invention also provides a gas extraction device for removing gas from an ionic liquid. The gas extraction device comprises a bubble capture chamber, a gas/liquid detector according to the invention and a bubble removal system. The bubble capture chamber is structured to accumulate a bubble of gas. At least one of the electrodes constituting the capacitative sensor of the gas/liquid detector is located in the bubble capture chamber and is shaped to substantially follow the perimeter of the bubble capture chamber. The capacitance detector of the gas/liquid detector generates an output signal that changes state when the bubble of gas accumulated in the bubble capture chamber has grown to a predetermined size and overlaps at least part of the capacitative sensor. The bubble removal system is coupled to the bubble capture chamber and operates in response to the output signal of the capacitance detector to extract the bubble of gas from the bubble capture chamber.

The invention also provides a pressure sensor for determining the pressure of an ionic liquid. The pressure sensor comprises a pressure-to-position converter and a gas/liquid detector according to the invention. The pressure-to-position converter is in pressure-communication with the liquid and is configured to establish a liquid surface whose position depends on the pressure of the liquid. At least one of the electrodes of the capacitative sensor of the gas/liquid detector is located to contact the liquid in the pressure-to-position converter. The fraction of the area of at the least one of the electrodes of the capacitative sensor that is in contact with the liquid depends on the position of the liquid surface.

Finally, the invention provides a gas/liquid detector for an ionic liquid. The gas/liquid detector comprises a capacitative sensor and a capacitance detector. The capacitative sensor includes a first electrode, a second electrode and Debye elements extant in the liquid adjacent such portions of the electrodes that are in contact with the liquid. The Debye elements each include a Debye capacitor with an associated shunt conductor. The shunt conductor has an exponentially-increasing conductance versus voltage characteristic. The Debye elements adjacent the first and second electrodes are connected in series by conduction through the liquid. The Debye element adjacent at least the first electrode has a substantially greater capacitance than the capacitance between the electrodes absent the Debye elements. The capacitance detector is connected to the capacitative sensor and measures the capacitance of the capacitative sensor by applying an alternating voltage between the electrodes. The alternating voltage has a voltage amplitude less than the voltage amplitude at which the Debye element extant adjacent at least the first electrode ceases to be predominantly capacitative.

By measuring the capacitance of the capacitative sensor with an alternating voltage having a voltage amplitude less than the voltage amplitude at which at least one of the Debye elements ceases to be predominantly capacitative, the capacitances measured are one or more orders of magnitude greater than the capacitances conventionally measured between electrodes in contact with a liquid. This enables the gas/liquid detector according to the invention to have a detection reliability and accuracy significantly higher than that of a conventional detector. In many cases, this also enables the gas/liquid detector according to the invention to use a capacitative sensor with a substantially smaller area than a conventional capacitative sensor.

BRIEF DESCRIPTION OF THE DRAWINGS

FIGS. 4A and 4B are respectively a plan view and a cross sectional view of a gas extraction device according to the invention incorporating two gas/liquid detectors according to the invention. The cover of the gas extraction device has been made transparent to show the inner structure of the device.

FIG. 4C is a view of the underside of the cover of the gas extraction device according to the invention showing the locations of the gas/liquid detectors.

FIG. 4D is an enlarged view of part of the capacitative sensor of one of the gas/liquid devices in the gas extraction device shown in FIGS. 4A–4C.

FIGS. 6A–6F are plan views illustrating the operation of the gas extraction device according to the invention. The cover of the gas extraction device has been made transparent to show the inner structure of the device.

FIGS. 8A and 8B are respectively a plan view and a cross sectional view of a gas extraction device according to the invention incorporating an embodiment of a gas/liquid detector according to the invention in which the capacitative sensor includes dissimilar electrodes. The cover of the gas extraction device has been made transparent to show the inner structure of the device.

FIG. 8C is an enlarged view of part of one of the electrodes constituting the capacitative sensor of one of the gas/liquid devices in the gas extraction device shown in FIGS. 8A and 8B.

DETAILED DESCRIPTION OF THE INVENTION

Figure 1A:
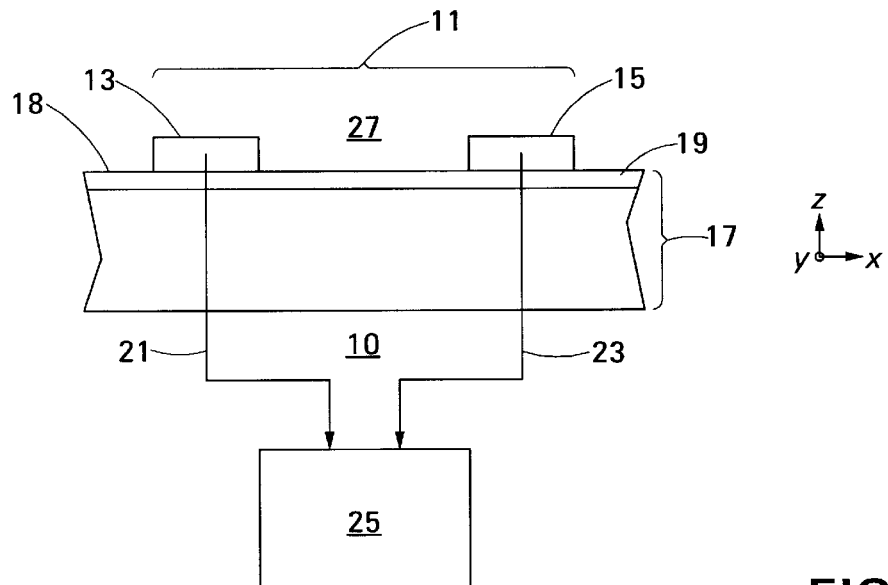
FIGS. 1A and 1B are side views of a first embodiment of a gas/liquid detector according to the invention in the absence of and in the presence of the liquid, respectively.

The invention is based on the observation that, when conductive electrodes are located in an ionic liquid, such as a solution of sodium bicarbonate in water or the types of inks typically used in ink-jet printers, an electrolytic cell is formed in the liquid adjacent each of the electrodes. The electrolytic cell has an internal voltage and an electric field that depends on the materials of the electrode and of the liquid. A diffuse double layer of charge exists in the electrolytic cell. The diffuse double layer of charge behaves as a capacitor with an associated shunt conductor. The diffuse double layer of charge will be called a Debye element. The capacitor constituting the Debye element will be called a Debye capacitor. A Debye capacitor is similar to an electrolytic capacitor having an equivalent plate spacing that scales with the barrier voltage of the diffuse double layer and the ion concentration at the electrode. The most convenient scaling is in terms of the Debye length $1/\kappa$ of the liquid. The Debye length is in the range from a few tens to a few hundreds of Ångstroms.

The ionic liquid is conductive and connects the Debye elements in series between the electrodes. Consequently, the electrical characteristics of the serial arrangement of the two Debye elements can be measured by connecting a measurement device to the electrodes. In particular, the capacitance of the capacitative component of the serial arrangement of the two Debye elements, i.e., the capacitance of the serial arrangement of two Debye capacitors, can be measured by connecting a capacitance detector to the electrodes.

The capacitance of a capacitor is inversely proportional to its plate spacing. Because the equivalent plate spacing of the Debye capacitors that exist on electrodes when the electrodes are in contact with an ionic liquid is much smaller than the physical distance between the electrodes, the capacitance per unit area between two electrodes in contact with an ionic liquid, calculated taking account of the capacitance of the Debye elements, is between several and many times greater than the capacitance per unit area conventionally calculated using the physical distance between the electrodes as the plate spacing and the dielectric constant of the ionic liquid. However, conventional ways of measuring the capacitance per unit area of electrodes in contact with an ionic liquid typically give capacitance values that agree with the conventionally-calculated capacitance values. Thus, conventional ways of measuring the capacitance of electrodes in contact with an ionic liquid fail to measure the capacitance of the Debye elements that exist on the electrodes when the electrodes are in contact with the liquid.

Conventional ways of measuring the capacitance of electrodes in contact in an ionic liquid fail to measure the capacitance of the serial arrangement of Debye elements because the Debye elements have characteristics that are non-linear with applied voltage. The capacitance of the Debye capacitor and the conductance of the associated shunt conductor are both voltage-dependent. In particular, the conductance of the shunt conductor increases exponentially with the applied voltage in manner similar to the way in which the conductance of a semiconductor diode increases exponentially with applied voltage. At an applied voltage typically greater than a few tens of millivolts, the shunt conductor has such a high conductance that it essentially short circuits the Debye capacitor. Conventional ways of measuring the capacitance of electrodes in contact in an ionic liquid typically apply an alternating signal with an amplitude of the order of one volt to the electrodes. A voltage of this order is many times greater than the applied voltage at which the shunt conductor essentially short circuits the Debye capacitor. Consequently, conventional measuring techniques fail to measure the capacitance of the Debye elements that exist on the electrodes.

The gas/liquid detector according to the invention measures the capacitance between the electrodes in a way that prevents the shunt conductor associated with each Debye capacitor from short circuiting the Debye capacitor, and therefore enables the capacitance of the Debye elements to be measured. As a result, when the electrodes are in contact with the ionic liquid, the gas/liquid detector according to the invention measures a capacitance per unit area of electrode one or more orders of magnitude greater than the conventionally-measured capacitance per unit area. This increased capacitance provides the gas/liquid detector according to the invention with many advantages over conventional gas/liquid detectors. These advantages include an increase in its detection reliability, a reduction of the area of its electrodes or a combination of these advantages.

Figure 1B:
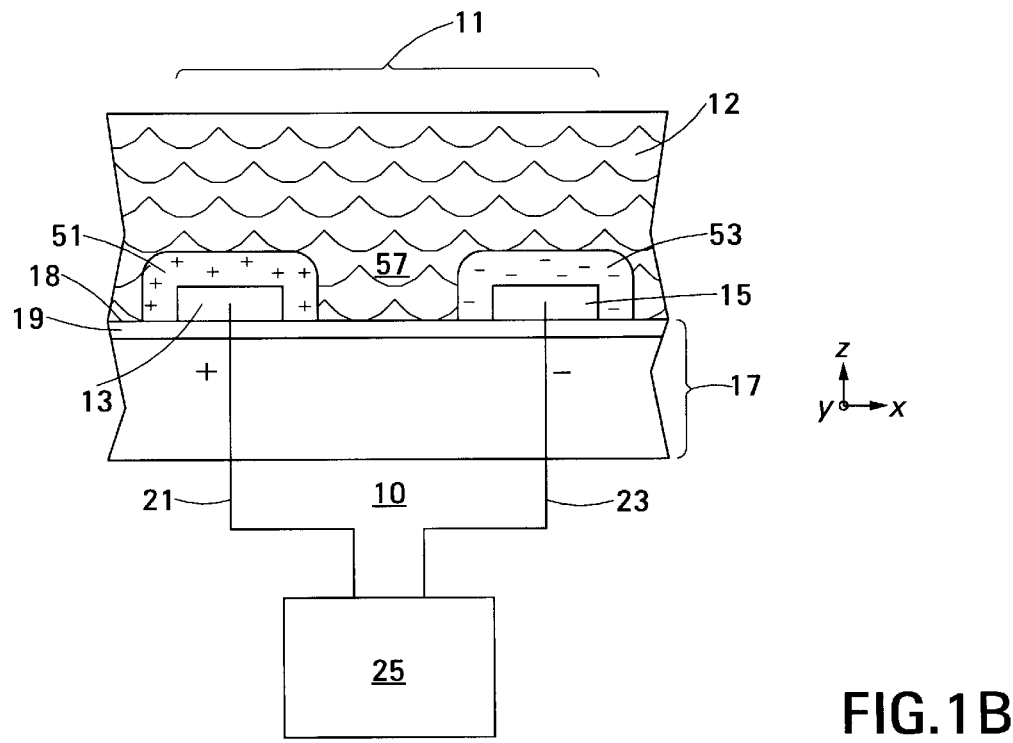

FIGS. 1A and 1B show a portion of a microfluidics device incorporating a simplified example 10 of a gas/liquid detector according to the invention. The gas/liquid detector according to the invention generates a signal that reliably indicates whether the sensor of the gas/liquid detector is in contact with a gas, or with an ionic liquid. The gas/liquid detector can also be configured to generate a signal that reliably indicates the fraction of the area of the sensor that is in contact with a liquid, or that is not in contact with the liquid.

The gas/liquid detector 10 is shown in the absence of a liquid in FIG. 1A, and in the presence of the liquid 12 in FIG. 1B. The gas/liquid detector 10 is composed of the capacitative sensor 11 and the capacitance detector 25. The capacitative sensor is positioned at the location in the microfluidics system where it is desired to perform gas/liquid detection. As used in this disclosure, the term gas/liquid detection encompasses detecting the presence of the liquid at the location, detecting the absence of the liquid at the location, detecting the presence of gas at the location, detecting the absence of gas at the location, and detecting the position of the surface between the gas and the liquid at the location.

The capacitive detector includes the electrodes 13 and 15 extending in the y-direction substantially parallel to one another. The capacitative sensor is supported by the substrate 17, and the capacitance detector is preferably formed near the capacitative sensor on and under the surface 18 of the substrate, although this is not critical to the invention. The substrate is shown as including the insulating layer 19 on which the capacitative sensor is located, although this layer can be omitted if the substrate is insulating.

The electrodes 13 and 15 constituting the capacitative sensor 11 are connected by suitable conductors shown schematically at 21 and 23 to the capacitance detector 25. The capacitance detector determines the capacitance between the electrodes 13 and 15 by applying an alternating or otherwise varying voltage between the electrodes. The characteristics of this voltage will be described below.

In the absence of liquid, shown in FIG. 1A, the capacitance of the capacitative sensor 11 depends on the effective areas of the electrodes 13 and 15, the inverse of the effective distance in the x-direction between the electrodes, and the dielectric constant of the gas 27 filling the space between the electrodes. The gas may be air or some other gas, and may include a vapor resulting from evaporation of part of the liquid 12. The dielectric constant of the gas 27 is close to unity. Since the distance between the electrodes in the x-direction is typically several microns, the capacitance of the capacitative sensor 11 measured by the capacitance detector 25 is relatively low. In some cases, when the area of the capacitative sensor 11 is small, the capacitance of the capacitative sensor in the absence of the liquid may be below the noise threshold of the capacitance detector.

When the liquid 12 comes into contact with the capacitative sensor 11, as shown in FIG. 1B, the voltages on the electrodes 13 and 15 cause the double diffuse layers of charge constituting the Debye elements 51 and 53, respectively, to form in the liquid adjacent the electrodes. At the instant shown in FIG. 1B, the capacitance detector 25 applies a positive voltage to the electrode 13 and a negative voltage to the electrode 15. The positive voltage on the electrode 13 attracts negative ions and repels positive ions (marked+) to form the diffuse double layer constituting the Debye element 51. The negative voltage on the electrode 15 attracts positive ions and repels negative ions (marked−) to form the diffuse double layer constituting the Debye element 53.

Figure 1C:
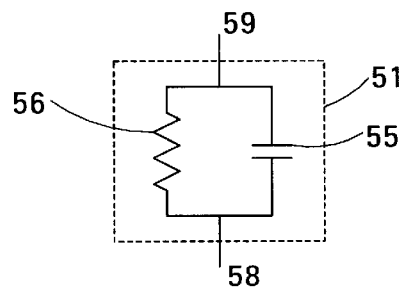
FIG. 1C is a schematic equivalent circuit of one of the Deybe elements shown in FIG. 1B.

FIG. 1C shows the equivalent circuit of the Debye element 51. The equivalent circuit of the Debye element 53 is similar and so will not be described. The Debye element includes the Debye capacitor 55 and the associated shunt conductor 56 connected in parallel with the Debye capacitor. The connection between the Debye element and the liquid 12 is shown at 59 and the connection between the electrode 13 and the Debye element is shown at 58. As noted above, the Debye element 51 is connected in series between the electrode 13 and the liquid. Also as noted above, the Debye capacitor 51 has an equivalent plate spacing that scales with the barrier voltage of the diffuse double layer and the ion concentration at the electrode. The most convenient scaling is in terms of the Debye length $1/\kappa$ of the liquid; see, for example, the Gouy-Chapman analysis of the diffuse double layers set forth in chapter 5 of A. W. Adamson & A. P. Gast, PHYSICAL CHEMISTRY OF SURFACES, John Wiley & Sons, New York, 1997. The Debye length is given by $\{(\in\in_0(kT/q))/qN\}^{1/2}$, where $\in$ is the relative permittivity, $\in_0$ is the permittivity of free space, k is Boltzmann's constant, q is the electronic charge, T is the absolute temperature, and N is ion concentration in the liquid. In a solution of sodium bicarbonate in tap water, the Debye length is in the range from several tens to a few hundred Ångstroms.

The shunt conductor 56 has a conductivity that increases substantially exponentially as the voltage applied across the conductor increases. The conductivity characteristic of the shunt conductor 56 is analogous to that of a semiconductor diode. Accordingly, at low values of the applied voltage, the shunt conductor has a low conductivity, and the Debye element 51 is predominantly capacitive, as measured between the terminals 58 and 59. However, as the applied voltage increases, the conductivity of the shunt conductor increases until at a certain applied voltage, the Debye element ceases to be predominantly capacitive and becomes predominantly conductive. Thus, to measure the capacitance of the Debye capacitor 55 reliably, the applied voltage across the Debye element 51 must have an amplitude in the range in which the Debye element is predominantly capacitive. The maximum of this range may correspond to the voltage at which the conductance of the shunt conductor falls to a level equal to the impedance of the Debye capacitor. Since this voltage depends on such variables as the ion concentration on the liquid, it is preferable to use an applied voltage that has an amplitude that is less, by an acceptable safety margin, than the maximum. Such a voltage may correspond to the voltage at which the conductance of the shunt conductor 56 becomes less than ten times the impedance of the Debye capacitor 55, for example. Other voltages in the range may alternatively be used, depending on the safety margin required, for example.

Thus, the capacitance detector 25 is configured to measure the capacitance of the capacitative sensor 11 by applying an alternating voltage having an amplitude that is less, by a suitable safety margin, than the voltage at which the Debye elements 51 and 53 that exist on the electrodes when the liquid 12 contacts the electrodes, as shown in FIG. 1B, cease to be predominantly capacitive. In a solution of sodium bicarbonate in tap water, for example, the applied voltage is preferably in the range of about 30 mV to about 100 mV, depending on the material of the electrodes and the concentration of ions in the water.

Referring once more to FIG. 1B, the region 57 of the ionic liquid 12 between the electrodes 13 and 15 is conductive and electrically connects the side of the Debye element 51 remote from the electrode 13 to the side of the Debye element 53 remote from the electrode 15. The other sides of the Debye elements 51 and 53 are in electrical contact with the electrodes 13 and 15, respectively. Thus, the liquid connects the Debye elements 51 and 53 in series between the electrodes 13 and 15.

Because the Debye capacitor of each of the Debye elements 51 and 53 has a capacitance that corresponds to a conventional capacitor with an inter-plate distance that is a small fraction of the physical distance between the electrodes 13 and 15, the capacitance of the serially-connected Debye elements shown in FIG. 1B, as measured by the capacitance detector 25, is many times that of the capacitor formed by the electrodes 13 and 15 and the gas dielectric shown in FIG. 1A. As a result, when the liquid 12 is present, the capacitance of the capacitive sensor 11 is greater than that in the absence of the liquid by a large factor that is easy for the capacitance detector 25 to detect.

In an alternative embodiment (not shown) the electrodes 13 and 15 constituting the capacitative sensor 11 are supported opposite one another by two different substrates. The substrates are separated by a gap through which the liquid can flow. Moreover, although the electrodes 13 and 15 are shown as having similar sizes and shapes and are described above as extending parallel to one another in the y-direction, the shape and relative orientation of the electrodes in this and the other embodiments described in this disclosure are not critical to the invention. The electrodes can have different sizes and shapes, and need not extend parallel to one another provided that they do not physically contact one another.

Although both of the electrodes 13 and 15 constituting the capacitative sensor 11 are described above as being positioned in the location in the microfluidics system where it is desired to perform gas/liquid detection, this is not critical to the invention. In other embodiments, to be described below, only one of the electrodes constituting the capacitative sensor is positioned at the location where it is desired to perform gas/liquid detection, and the other of the electrodes constituting the capacitative sensor is located in permanent contact with the liquid elsewhere in the microfluidics system.

Figure 2A:
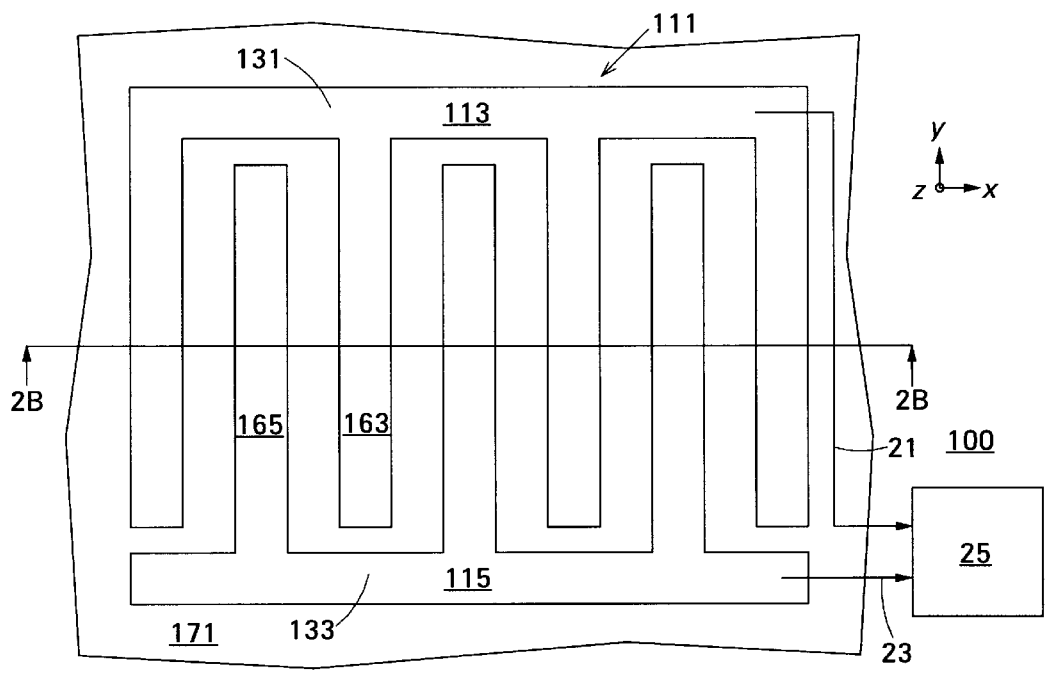
FIG. 2A is a plan view of a second embodiment of a gas/liquid detector according to the invention.
Figure 2B:
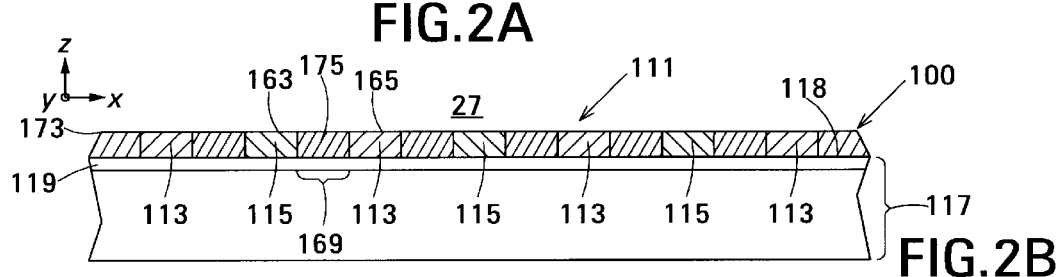
FIGS. 2B and 2C are side views of the second embodiment of the gas/liquid detector according to the invention in the absence of and in the presence of the liquid, respectively.
Figure 2C:
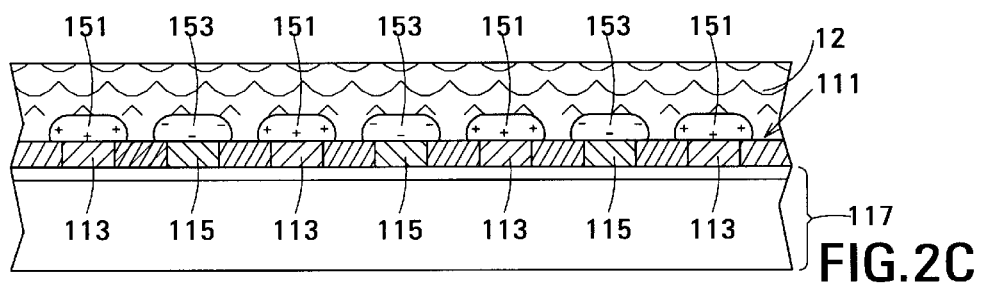
Figure 2D:
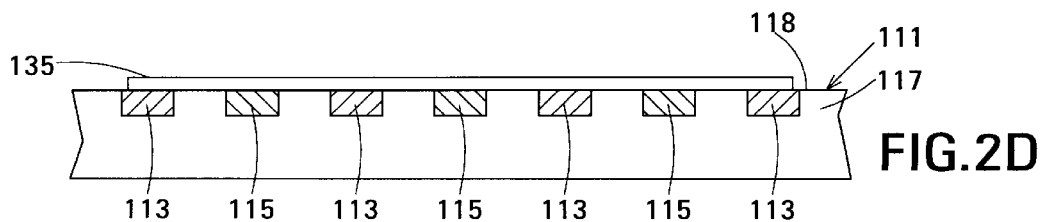
FIG. 2D is a side view of a variation on second embodiment of the gas/liquid detector according to the invention in which the capacitative sensor has a modified electrode structure. The detector is shown in the absence of the liquid.

The large capacitance per unit area of the serially-connected Debye elements 51 and 53 enables the structure shown in FIGS. 1A and 1B to form the basis of a smallarea gas/liquid detector that has a capacitance sufficiently large to be measured easily and reliably using a simple capacitance detector 25. A simplified example of a practical embodiment of such a gas/liquid detector is shown in FIGS. 2A–2C. FIG. 2A is a plan view and FIGS. 2B and 2C are cross-sectional views of the gas-liquid detector 100 located on a portion of the substrate 117 of a microfluidics device. The gas/liquid detector is shown in the absence of a liquid in FIG. 2B, and in the presence of a liquid 12 in FIG. 2C. An alternative embodiment is shown in FIG. 2D. Elements of the embodiment shown in FIGS. 2A–2D that correspond to elements of the embodiment shown in FIGS. 1A and 1B are indicated using the same reference numerals and will not be described again in detail here.

Referring first to FIGS. 2A and 2B, the gas/liquid detector 100 is composed of the capacitative sensor 111 and the capacitance detector 25. The capacitative sensor is positioned at the location in the microfluidics system where it is desired to perform gas/liquid detection. The capacitative sensor includes the electrodes 113 and 115 that are comb-shaped and are interleaved with one another so that adjacent fingers of the electrodes extend in they-direction substantially parallel to one another. The Figures show the exemplary fingers 163 and 165 of the electrodes 113 and 115, respectively. The fingers of the electrode 113 are interconnected by the connecting portion 131, and the fingers of the electrode 115 are interconnected by the connecting portion 133. The capacitative sensor is supported by the substrate 117, and the capacitance detector is preferably formed near the capacitative sensor on and under the surface 118 of the substrate, although this is not critical to the invention. The substrate is shown as including the insulating layer 119 on which the electrodes are located, although this layer can be omitted if the substrate is fabricated from an insulating material.

The electrodes 113 and 115 each have a thickness in the z-direction and extend in the z-direction from the surface of the substrate 117. The electrodes and the surface 118 of the substrate define a recess. The portion of the recess that exists between the fingers 163 and 165 and the surface 118 is shown at 169. In some embodiments with some types of the liquid 12, the surface tension of the liquid can trap part of the liquid in the recess after most of the liquid has receded from contact with the capacitative sensor 111. This liquid can cause the gas/liquid detector to indicate the presence of the liquid when the liquid is not in fact in contact with most of the capacitative sensor. In embodiments in which retention of the liquid between the electrodes is a problem, the capacitative sensor can include the planarizing layer 171 that at least partially fills the recess between the electrodes. The portion of the planarizing layer that fills the recess 169 between the fingers 163 and 165 is shown at 175. The drawings show the planarizing layer filling the recess flush with the surface 173 of the electrodes, but the planarizing layer may alternatively only partially fill the recess.

The electrodes 113 and 115 constituting the capacitative sensor 111 are connected by suitable conductors shown schematically at 21 and 23 to the capacitance detector 25. The capacitance detector determines the capacitance between the electrodes 113 and 115 by applying an alternating or otherwise varying voltage between the electrodes. The voltage applied has an amplitude less than voltage at which the Debye elements 151 and 153 that exist on the electrodes when the liquid 12 contacts the electrodes, as shown in FIG. 2C, cease to be predominantly capacitative, as described above.

In the absence of liquid, shown in FIG. 2B, the capacitance of the capacitative sensor 111 depends on the effective areas of the electrodes 113 and 115, the inverse of the effective distance in the x-direction between the electrodes, and the dielectric constants of the material of the planarizing layer 171 (if present) and of the gas 27 overlaying the electrodes. The gas may be air or some other gas, and may include a vapor resulting from part of the liquid 12 evaporating. The dielectric constant of the gas 27 is close to unity. Since the distance between the electrodes in the x-direction is of the order of microns, the capacitance of the capacitative sensor 111 measured by the capacitance detector 25 is relatively low. The area of the capacitative sensor can be made so small that the capacitance of the capacitative sensor in the absence of the liquid may be below the noise threshold of the capacitance detector.

When the liquid 12 comes into contact with the capacitative sensor 111, as shown in FIG. 2C, the voltages on the electrodes 113 and 115 cause the diffuse double layers constituting the Debye elements 151 and 153, respectively, to form in the liquid adjacent the electrodes. At the instant shown in the Figure, the capacitance detector 25 applies a positive voltage to the electrode 113 and a negative voltage to the electrode 115. The positive voltage on the electrode 113 attracts negative ions and repels positive ions (marked+) to form the diffuse double layer constituting the Debye element 151. The negative voltage on the electrode 115 attracts positive ions and repels negative ions (marked−) to form the diffuse double layer constituting the Debye element 153. As shown in FIG. 1C, each Debye element behaves as a Debye capacitor with an associated shunt conductor. A Debye capacitor is similar to an electrolytic capacitor, and has an equivalent plate spacing that scales in accordance with the Debye length $1/\kappa$ of the liquid, which is in the range from a few tens to a few hundreds of Ångstroms.

The ionic liquid 12 is conductive and electrically connects the side of the Debye element 151 remote from the electrode 113 to the side of the Debye element 153 remote from the electrode 115. The other sides of the Debye elements are electrically connected to the electrodes 113 and 115. Thus, the liquid connects the Debye elements 151 and 153 in series between the electrodes 113 and 115, and the capacitance detector 25 detects a substantial capacitance between the electrodes 113 and 115 when the liquid 12 is in contact with the capacitative sensor 111.

As noted above, the example shown in FIGS. 2A–2C is simplified to simplify the drawings. In one embodiment of the capacitative sensor 111 fabricated to test the invention, the electrode 113 had 29 fingers similar to the finger 163, each 5 $\mu$m wide and about 200 $\mu$m long, and the electrode 115 had 28 fingers similar to the finger 165, each 5 $\mu$m wide and about 200 $\mu$m long. The fingers were separated by a gap of 5 $\mu$m, although the dimensions of gap were not critical. Overall, the capacitative sensor occupied an area of about 220×560 $\mu$m on the substrate 117. A capacitance meter that applied an a.c. signal of 35 mV rms at a frequency of 1 MHZ was used to measure the capacitance of the capacitative sensor. The measured capacitance changed by about 1 pF when a layer of de-ionized water was applied to the capacitative sensor, and by about 150 pF when a layer of an almost saturated solution of sodium bicarbonate in water was applied to the capacitative sensor. A similar capacitance change was measured when a layer of ink was applied to the capacitative sensor. The ink was of the type used in a popular range of ink-jet printers sold by the assignee of this disclosure. The frequency of the a.c. signal was not critical: similar values of the capacitance change were obtained at frequencies of 100 kHz and 10 kHz.

Since capacitance changes of about 10 pF can be measured reliably using relatively simple capacitance detectors, gas/liquid detection using the embodiment just described has a significant margin of reliability. Alternatively, gas/liquid detectors with an acceptable, albeit lower, margin of reliability can be made with capacitative sensors having an area less than one-tenth of that of the embodiment just described. Such detectors have linear dimensions less than one-third of those set forth above. Further reductions in the area of the capacitative sensor can be obtained by reducing the gap between the electrodes, which enables the effective area of the electrodes to be increased in a sensor of given dimensions.

The liquid/gas detector 100 is preferably made using micromachining techniques. Such techniques are well known in the art and so will not be described in detail here. The substrate 117 is part of a wafer of silicon or some other suitable semiconducting or insulating material. The insulating layer 119, if required, may be a layer of silicon dioxide, silicon nitride or other suitable insulator grown or deposited on the surface of the wafer. The electrodes 113 and 115 can be made from a metal or a semiconductor, such as doped polysilicon or tantalum nitride, located on the surface of the substrate 117. Techniques for creating interleaved electrode structures using such materials are known in the art and will therefore not be described here. Polyimide can be used as the planarizing layer 171 when such a layer is additionally included.

Good results were obtained with the electrodes 113 and 115 made from a tantalum-aluminum alloy or from sputtered tantalum nitride. Ohmic conduction between the electrodes and the liquid 12 was small when the electrodes were made of these materials. Oxidizing metals, such as aluminum or tantalum, and alloys including oxidizing metals may also be suitable materials for the electrodes. Significant ohmic conduction between the electrodes and the liquid occurred when tests were performed using electrodes made of gold. Similar results are likely with electrodes made from other low work function materials. However, this observation is used to advantage in the embodiment described below with reference to FIGS. 8A–8C.

Electrochemical interaction between the liquid 12 and the material of the electrodes 113 and 115 can be prevented by covering the surface 173 of the electrodes with a very thin passivating layer (not shown). This layer may be a layer of silicon dioxide or silicon nitride less than about 50 Å thick.

As an alternative to locating the electrodes constituting the capacitative sensor 111 on the surface of the substrate 117, the electrodes may be formed in the substrate 117. Forming the electrodes in the substrate has the advantage of providing an inherently planar surface without the need for the additional planarizing layer 171. An embodiment having an inherently planar surface is shown in FIG. 2D. The substrate 117 is a wafer of a semiconductor material such as silicon. The electrodes 113 and 115 constituting the capacitative sensor 111 are made by introducing a high concentration of impurities into selected areas of the surface of the substrate. The selected areas define the shape of the electrodes. The electrodes are preferably comb-shaped and are interleaved as shown in FIG. 2A.

The substrate 117 may be part of a wafer of silicon, for example. The silicon may be intrinsic or may be doped with a low concentration of acceptor (p-type) impurities. The electrodes are defined by diffusing a high concentration of a donor (n-type) impurity into the surface 118 of the substrate through a suitable mask. The resulting n+ regions constitute the electrodes 113 and 115. The electrodes may alternatively be defined by forming regions having a high concentration of an acceptor impurity. The impurities may be introduced by diffusion, ion implantation or in other ways.

A layer of metal is applied to the part of the surface of each n+ region formed in the substrate 117 to form metal contacts that make electrical contact to the electrodes 113 and 115. The metal contact of each electrode is preferably located on the region of the electrode that interconnects the fingers of the electrode. This region corresponds to the regions 131 and 133 of the electrodes 113 and 115, respectively, of the embodiment shown in FIG. 2A. The metal contact 135 located on the region 131 (FIG. 2A) of the electrode 113 is shown in FIG. 2D. The metal contacts are connected via conductors similar to the conductors shown schematically at 21 and 23 to the capacitance detector 25 (FIG. 2A).

Since the surface 118 of the substrate 117 remains substantially planar after the regions defining the electrodes 113 and 115 have been formed by introducing impurities, and since the metal contacts applied to the electrodes are spaced apart by the length of the fingers of the electrodes, this embodiment lacks topological features that can trap portions of the liquid that can give rise to false detections of the presence of the liquid.

The surface 118 of the substrate 117 may be covered with a very thin passivating layer (not shown). This layer may be a layer of silicon dioxide or silicon nitride less than about 50 Å thick.

Referring once again to FIG. 2A, the capacitance detector 25 can be fabricated from bipolar or field-effect transistors formed in and on the substrate 117, or may be remotely located. Circuits for generating an analog or digital signal in response to a change of capacitance are well known in the art and will therefore not be given here. One example of a suitable circuit, which measures the capacitance of the capacitative sensor 111 by measuring the impedance of the sensor, is shown in FIG. 3.

Figure 3:
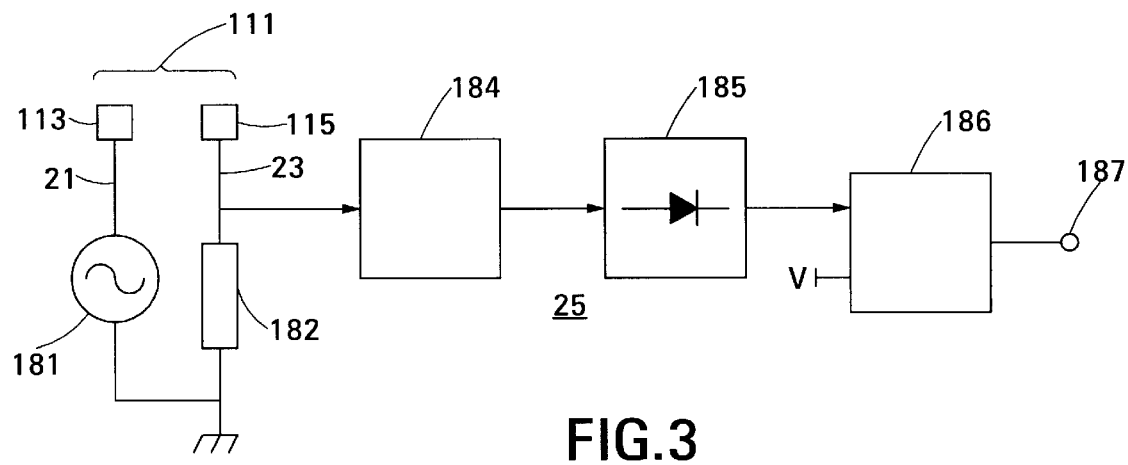
FIG. 3 is a schematic diagram of an example of the capacitance detector of the gas/liquid detector according to the invention.

In the circuit shown in FIG. 3, the conductor 21 connects the electrode 113 of the capacitative sensor 111 to the oscillator 181. The oscillator generates an a.c. signal having a maximum amplitude less, by a suitable safety margin, than the voltage at which the Debye elements 151 and 153 that exist on the electrodes when the electrodes are in contact with an ionic liquid, as shown in FIG. 2C, cease to be predominantly capacitive. This voltage depends on the material of the electrodes and on the pH and the constituents of the mixture making up the liquid. In the practical embodiments described above, the signal generated by the oscillator had a frequency of 1 MHZ, but the value of the frequency is not critical. The applied voltage was less than 100 mV peak.

The conductor 23 connects the electrode 115 to the impedance 182 and to the input of the amplifier 184. The impedance 182 has a impedance comparable with that of the capacitative sensor 111 when the capacitance sensor is in contact with a layer of the liquid 12 (FIG. 2C). For example, when the impedance of the above-described practical embodiments was measured at a frequency of 1 MHZ, the impedance 182 was a resistor having a resistance of 1 kΩ. The appropriate impedance of the impedance 182 scales inversely with the measurement frequency. Moreover, a capacitor, or a series or parallel arrangement of a capacitor and a resistor may be used as the impedance 182.

The output of the amplifier 184 is connected to the rectifier 185, and the output of the rectifier is connected to a first input of the comparator 186. The comparator also has a second input through which it receives the reference voltage V.

The impedance of the capacitative sensor 111 and that of the impedance 182 form a divider that attenuates the output voltage of the oscillator 181. When the capacitative sensor is not in contact with the liquid 12, the impedance of the capacitative sensor is high, and the input voltage to the amplifier 184 is therefore substantially smaller than the output voltage of the oscillator. When the liquid 12 contacts the capacitative sensor, the impedance of the capacitative sensor drops significantly, and the input voltage to the amplifier increases substantially.

The amplifier 184 amplifies the output of the divider formed by the capacitative sensor 111 and the impedance 182, the rectifier 185 generates a DC voltage in response to the output of the amplifier, and the comparator 186 compares the DC voltage with the reference voltage V. The state of the output of the comparator depends on the whether the DC voltage generated by the rectifier is greater than or less than the reference voltage. By appropriately choosing the value of the impedance 182 in relationship to the impedance of the capacitative sensor 111 at the frequency of the signal generated by the oscillator 181, and by choosing the gain of the amplifier 184 and the value of the reference voltage V, the state of the output 187 of the comparator can be made to depend on whether or not the capacitative sensor 111 is in contact with the liquid 12.

The comparator 186 can be provided with a second reference voltage so that the output 187 can be made to change state at different impedances of the capacitative sensor 111, depending on whether the impedance of the capacitative sensor is increasing or decreasing. This provides the capacitative detector 25 with hysteresis. As a further alternative, the comparator can be omitted, and the output signal of the rectifier 185 can be used as an analog signal related to the capacitance of the capacitative sensor. Such an analog signal can be used if an indication of the fraction of the area of the capacitative sensor that is in contact with the liquid is required, for example. A more precise measurement of the capacitance of the capacitative sensor, and, hence of the fraction of the area of the capacitative sensor in contact with the liquid, can be made by connecting the capacitative sensor to one arm of a selfbalancing automatic switched-capacitor capacitance measurement bridge.

Many other suitable circuits that can be used as the capacitance detector 25 are known in the art, and so alternative circuits will not be described here.

The application of a gas/liquid detector according to the invention to control an embodiment 202 the gas extraction device described in the above-mentioned simultaneously-filed patent application is shown in FIGS. 4A–4D. The gas extraction device is composed of a bubble capture chamber and a gas removal system. Gas removed from the ink passing through the ink delivery channel is accumulated in the bubble capture chamber. The bubble removal system is composed of a primary extraction chamber and a secondary extraction chamber and their associated extraction heaters, and extracts the bubbles of gas from the bubble capture chamber to the exhaust manifold.

In the embodiment shown, the gas/liquid detector 200 includes the annular capacitative sensor 211 located in the bubble capture chamber 204 and is used to determine when a gas bubble of sufficient size has accumulated in the bubble capture chamber. A control circuit, to be described below, that forms part of the gas extraction device activates the primary extraction heater of the gas extraction device in response to a control signal generated by the gas/liquid detector 200. Activation of the primary extraction heater removes the bubble from the bubble capture chamber to the primary extraction chamber 110.

The gas extraction device 202 also comprises the gas/liquid detector 300 including the annular capacitative sensor 311 located in the primary extraction chamber 110. The gas/liquid detector 300 is used to determine when a gas bubble of sufficient size has accumulated in the primary extraction chamber. The above-mentioned control circuit activates the secondary extraction heater 128 of the gas extraction device in response to a control signal generated by the gas/liquid detector 300. Activation of the secondary extraction heater removes the bubble from the primary extraction chamber to the exhaust manifold 130.

The exemplary embodiment 202 of the gas extraction device shown in FIGS. 4A–4C is located in the ink delivery system of an ink-jet printer (not shown) and includes the gas release heater 140 or some other element that releases from the ink passing through the ink delivery channel 250 a gas, such as air, dissolved in the ink. The ink may pass through the ink delivery channel on its way to, or in, the print head of an ink-jet printer, for example. The gas/liquid detector according to the invention can also be incorporated in a gas extraction device that lacks a gas release heater or other gas-releasing element. Such a gas extraction device can be located at a point in the ink delivery system where bubbles of gas released from the ink accumulate. Such gas could be released from the ink by the ink firing element, for example, or by environmental changes. Irrespective of the way in which gas is released from the ink, the gas extraction device removes the bubbles of gas from the bubble capture chamber and transfers them to the exhaust manifold 130, thus removing the bubbles of gas from the ink delivery system.

The gas extraction device 202 extends between the ink delivery channel 250 and the exhaust manifold 130, and is composed of the primary extraction chamber 110, the secondary extraction chamber 120 and the primary and secondary extraction heaters 118 and 128. Ink flows through the ink delivery channel 250 between the ink inlet 52 and the ink outlet 54. The bubble capture chamber 204 is located in the ink delivery channel and is delineated from the ink delivery channel by an arrangement of pillars. In the example shown in FIGS. 4A–4C, the periphery of the bubble capture chamber is defined by an arrangement of five pillars 292–296, each having a circular cross section in the plane parallel to the surface 150 of the substrate 102. The pillars are approximately located on a segment of a circle.

The pillars 292–296 delineating the bubble capture chamber 204 from the ink delivery channel 250 are spaced and dimensioned to allow ink flowing through the ink delivery channel from the ink inlet 52 to the ink outlet 54 also to flow freely through the bubble capture chamber 204. The ink that flows through the bubble capture chamber comes into contact with the gas release heater 140. Heat generated by the gas release heater releases dissolved gas from the ink to generate a bubble (not shown) that gradually grows in size.

The primary extraction chamber 110 is coupled to the part of the ink delivery channel 250 that includes the bubble capture chamber 204. The primary extraction chamber is composed of the narrow, parallel-sided neck 112 in series with the tapered chamber 114. The tapered chamber 114 has a cross-sectional area that increases with increasing distance from the neck 112. The substantially semi-circular portion 116 of the tapered chamber 114 extends from the widest part of the tapered chamber, remote from the neck 112. The neck 112 connects the narrow end of the tapered chamber 114 to the bubble capture chamber.

The secondary extraction chamber 120 is located between the primary extraction chamber 110 and the exhaust manifold 130. The secondary extraction chamber has a structure similar to that of the primary extraction chamber. Elements of the secondary extraction chamber that correspond to elements of the primary extraction chamber are indicated by the same reference numerals with 10 added and will not be individually described.

The ink delivery channel 250, and the primary and secondary extraction chambers 110 and 120 are formed using conventional micromachining techniques in the layer of barrier material 152 located on the surface 150 of the substrate 102.

The exhaust manifold 130 extends from the end of the tapered chamber 124 remote from the neck 122 through the thickness of the substrate 102 into direct or indirect communication with the atmosphere. The exhaust manifold provides a path for the gas removed from the ink delivery channel 250 to vent to the atmosphere. The exhaust manifold may alternatively extend through the thickness of the cover 154.

Energy must be supplied to the gas extracted from the ink to move the gas from the bubble capture chamber 204 to the exhaust manifold 130 against the pressure difference between the ink pressure in the ink delivery channel 250 and atmospheric pressure in the exhaust manifold. The ink pressure in the ink delivery channel is less than atmospheric pressure. This energy is supplied in the form of heat generated by the primary extraction heater 118 located on the part of the substrate 102 that provides the floor of the primary extraction chamber 110. Additional energy is provided by the secondary extraction heater 128 located on the part of the substrate 102 that provides the floor of the secondary extraction chamber 120. Each heater is elongate and extends lengthways along the center line of the respective extraction chamber.

The gas release heater 140 is located on the part of the substrate 102 that provides the floor of the bubble capture chamber 204. The gas release heater is structurally similar to the heaters 118 and 128. The gas release heater warms the ink flowing through the ink delivery channel 250 to cause the ink to release gas, such as air, dissolved in the ink. The released gas collects in a bubble that is confined to the bubble capture chamber. As noted above, the gas release heater is optional.

Figure 5:
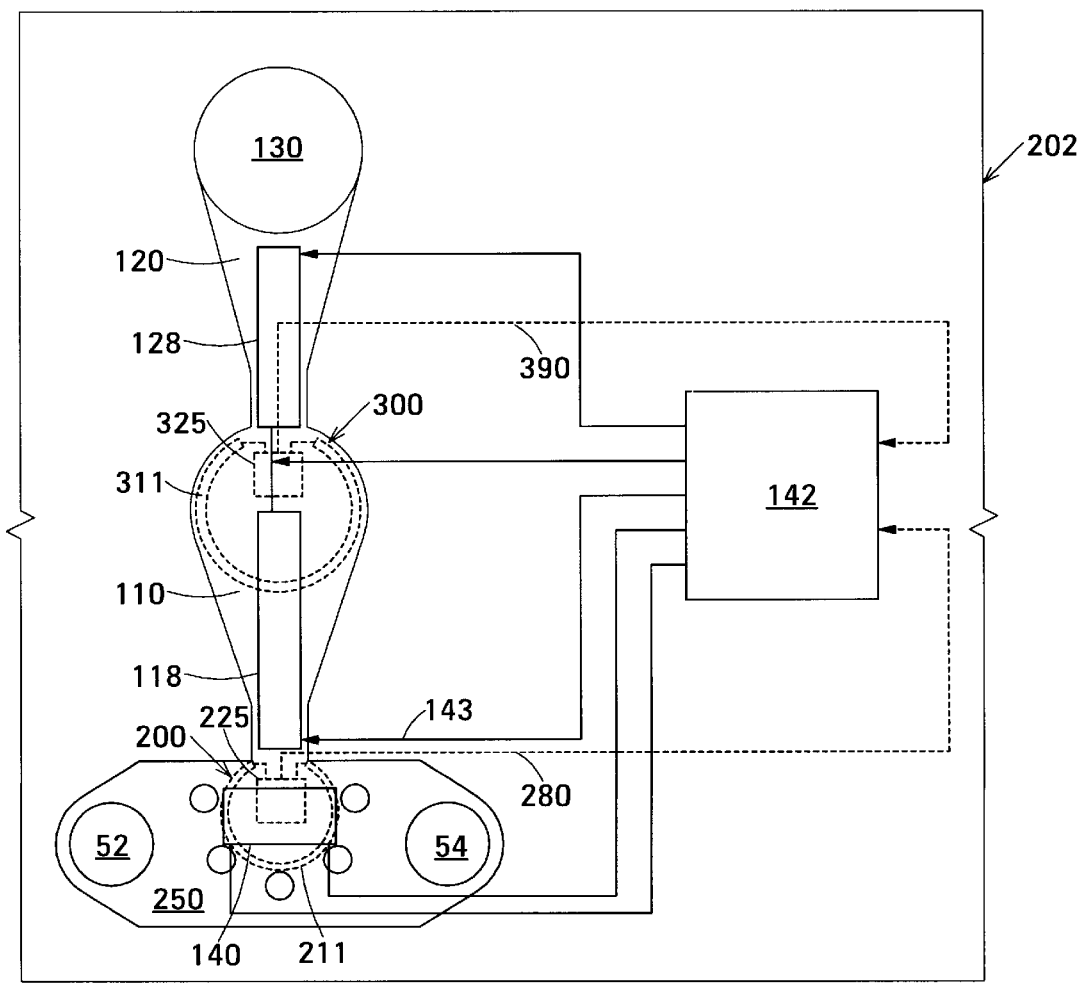
FIG. 5 s a schematic drawing showing the electrical arrangement of the gas extraction device according to the invention shown in FIGS. 4A–4C.

The electrical arrangement of the gas extraction device 202 is shown schematically in FIG. 5. The heaters 118, 128 and 140 are resistors connected to the controller 142 by conductive tracks located on the surface 150 of the substrate 102. An exemplary track connecting the controller to the heater 118 is shown schematically at 143. Although the controller may be physically separate from the substrate 102, and connected thereto by conductors such as wires, the controller is preferably built on and under the surface 150 of the substrate using conventional semiconductor circuit fabrication techniques.

The controller 142 selectively passes respective electric currents through the resistors constituting the heaters 118, 128 and 140. The electric currents cause the heaters to generate heat. In a preferred embodiment, the controller supplies current to the ejection heaters 118 and 128 in a series of ten 5 ms-wide pulses, with 5 ms between consecutive pulses. Pulsing the current supplied to the heaters reduces the transfer of heat from the heaters to the substrate 102, and maintains a clear temperature differential between the heaters and the part of the substrate adjacent the heaters.

Although the controller 142 may be an open-loop controller that feeds current to the heaters 118, 128 and 140 at pre-determined times for pre-determined durations in some embodiments of the gas extraction device, in the gas extraction device 202 shown in FIGS. 4A–4C, the controller operates in response to one or more gas/liquid detectors according to the invention. In the example shown, the gas extraction device 202 incorporates the gas/liquid detector 200 located in the bubble capture chamber and the gas/liquid detector 300 located in the primary extraction chamber 110. The gas/liquid detectors are shown as being located on the surface 132 of the cover 154 that forms the ceiling of the ink delivery channel 250 and of the primary and secondary extraction chambers 110 and 120. However, the location of the gas/liquid detectors on the surface of the cover is not critical to the invention. The gas/liquid detectors may alternatively be located on the surface 150 of the substrate 102, for example.

FIG. 4C shows the surface 132 of the cover 154 that faces into the ink delivery channel 250 and the primary and secondary extraction chambers 110 and 120. The locations with respect to the cover of the peripheries of the various elements of the gas extraction device 202 are shown by broken lines and the elements are identified by the same reference numerals as in FIGS. 4A and 4B. The capacitative sensor 211 of the gas/liquid detector 200 is located on the part of the surface 132 of the cover 154 that provides the ceiling of the bubble capture chamber 204. The capacitance detector 225 is preferably formed on and under the surface 132 of the cover, adjacent the capacitative sensor 211, although this is not critical to the invention. The capacitative sensor 311 of the gas/liquid detector 300 is located on the part of the surface 132 of the cover 154 that provides the ceiling of the primary extraction chamber 110. The capacitance detector 325 is preferably formed on and under the surface 132 of the cover adjacent the capacitative sensor 311, although this is not critical to the invention.

The capacitative sensor 211 will now be described. The electrodes 213 and 215 constituting the capacitative sensor are curved to follow the periphery of the bubble capture chamber 204 defined by the pillars 292–296. Alternatively, the electrodes may be slightly inset from the perimeter. As in the embodiment described above with reference to FIGS. 2A–2C, the electrodes 213 and 215 are comb-shaped and are interleaved with one another so that adjacent fingers of the electrodes are substantially concentric with one another. FIG. 4D shows the exemplary fingers 263 and 265 of the electrodes 213 and 215, respectively and the connecting portion 231 that interconnects the fingers of the electrode 213. FIG. 4D also shows part of the planarizing layer 271 between the fingers 263 and 265. However, the planarizing layer may be omitted in most embodiments.

The capacitative sensor 211 is supported by the cover 154. The cover is fabricated from a semiconductor material such as silicon, or an insulator. The cover includes a layer of an insulating material (not shown) adjacent the surface 132 on which the capacitative sensor is located. However, this insulating layer may not be necessary if the cover is fabricated from an insulating material. The recess defined by adjacent fingers of the electrodes 213 and 215 and the surface 132 of the cover is filled with the planarizing layer 271 that prevents portions of the ink from becoming trapped between adjacent ones of the fingers.

The capacitative sensor 311 is similar in structure to the capacitative sensor 211, and will therefore not be described in detail. The electrodes (not shown) of the capacitative sensor 311 are curved to follow a segment of a circle that is concentric with the semicircular portion 116 of the tapered chamber 114. Part of the periphery of the capacitative sensor 311 is located at, or may be slightly inset from, the periphery of the semicircular portion 116.

In the gas/liquid detector 200, the capacitative sensor 211 is connected to the capacitance detector 225 by conductors shown schematically at 221 and 223. The circuit shown in FIG. 3 may be used as the capacitance detector 225, for example. FIG. 5 schematically shows the conductor 280 that feeds the output signal generated by the capacitance detector to the control circuit 142.

In the gas/liquid detector 300, the connections between the capacitative sensor 311, the capacitance detector 325 and the control circuit 142 are similar to those just described.

The capacitance detectors 225 and 325 are configured to apply a voltage between the electrodes 213 and 215 and between the electrodes of the capacitative sensor 311 that has an amplitude that is less, by a suitable safety margin, than the voltage at which the Debye elements that exist on the portions of the electrodes in contact with the ink cease to be predominantly capacitative.

Operation of the gas extraction device 202 just described in response to the gas/liquid detectors 200 and 300 according to the invention will now be described with reference to FIGS. 5 and 6A–6F. To simplify FIGS. 6A–6F, the capacitance detectors 225 and 325 and the control circuit 142, and the conductors connecting the control circuit to the heaters and the capacitance detectors, as shown in FIG. 5, have been omitted. In addition, the ink is not shown.

In FIG. 6A, ink flows through the ink delivery channel 250 from the ink inlet 52 to the ink outlet 54. The ink fills the ink delivery channel and the primary and secondary extraction chambers 110 and 120. The control circuit has begun supplying current to the gas release heater 140, but no gas bubble has yet formed in the bubble capture chamber 204. In the gas/air detector 200 located in the bubble capture chamber 204, the entire area of the capacitative sensor 211 is in contact with the ink. Consequently, Debye elements exist over the entire areas of the electrodes constituting the capacitative sensor in a manner similar to that shown in FIG. 2C. The capacitance of the capacitative sensor, as detected by the capacitance detector 225, is high, and the output of the capacitance detector is in a first state that inhibits operation of the primary extraction heater 118.

In the gas/air detector 300 located in the primary extraction chamber 110, the entire area of the capacitative sensor 311 is in contact with the ink so that Debye elements exist over the entire areas of the electrodes constituting the capacitative sensor in a manner similar to that shown in FIG. 2C. The capacitance of the capacitative sensor 311, as detected by the capacitance detector 325, is high, and the output of the capacitance detector is in a first state that inhibits operation of the secondary extraction heater 128.

The gas release heater 140 heating the ink flowing through the ink delivery channel 250 releases dissolved gas, which accumulates to form the bubble 260 as shown in FIG. 6B. The flow of ink through the bubble capture chamber 204 traps the bubble against the pillars, for example, the pillar 296, which define the downstream boundary of the bubble capture chamber. The bubble overlaps the portion 246 of the capacitative sensor 211 so that this portion of the capacitative sensor is in contact with the gas contained in the bubble. No Debye elements exist in the portion 246 of the capacitative sensor. Consequently, the capacitance of the capacitative sensor, as detected by the capacitance detector 225, is less than that detected in FIG. 6A. However, the capacitance is still relatively high because the portion 246 is a relatively small fraction of the area of the capacitative sensor. Consequently, the output of the capacitance detector remains in the first state that inhibits operation of the primary extraction heater 118. Also, the gas/air detector 300 continues to inhibit operation of the secondary extraction heater 128.

As additional gas accumulates in the bubble 260 and the bubble grows, the size of the portion 246 of the capacitative sensor in contact with the gas contained in the bubble increases. Consequently, the capacitance of the capacitative sensor 211, as detected by the capacitance detector 225, progressively falls. FIG. 6C shows the gas extraction device after the bubble 246 has grown to fill the bubble capture chamber 204 and the bubble is ready for removal from the bubble capture chamber. When the bubble fills the bubble capture chamber, all or most of the area of the capacitative sensor 211 is in contact with the gas contained in the bubble. Debye elements exist on little or none of the area of the capacitative sensor. Consequently, the capacitance of the capacitative sensor, as detected by the capacitance detector, is significantly smaller than that detected in FIGS. 6A and 6B.

The capacitance detector 225 is configured so that the capacitance of the capacitative sensor 211 falling to the level corresponding to the bubble 260 covering most of the capacitative sensor, as shown in FIG. 6C, causes its output to change state to a second state. In response to the change in state of the output of the capacitance sensor, the control circuit 142 feeds current to the primary extraction heater 118. The gas/air detector 300 continues to inhibit operation of the secondary extraction heater 128.

Figure 6F:
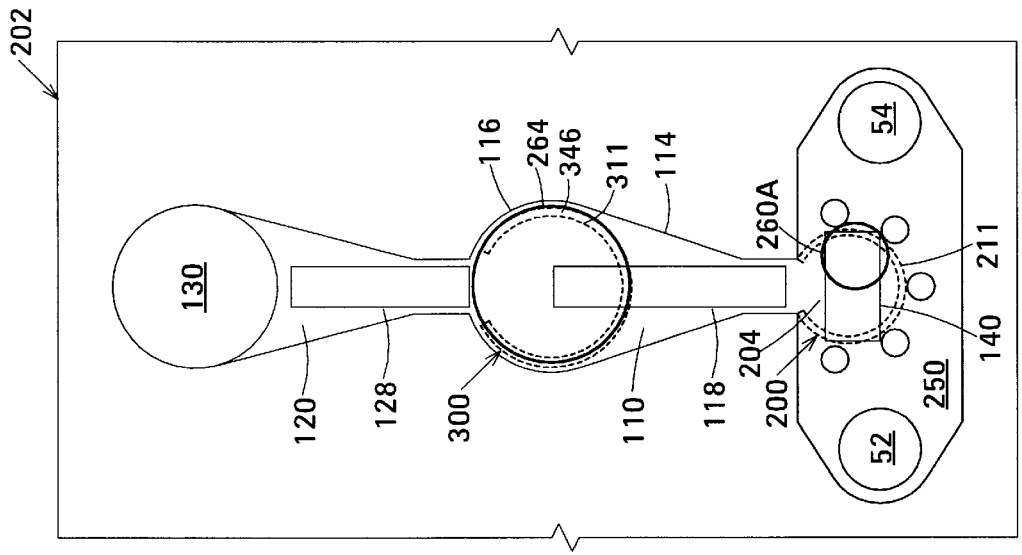

The primary extraction heater 118 heats the ink in the primary extraction chamber 110 to boiling point. The resulting ink vapor forms the vapor bubble 262 that grows explosively, as shown in FIG. 6D, and quickly encounters the walls of the tapered chamber 114. Contact between the vapor bubble and the walls of the tapered chamber causes the vapor bubble to move towards the wider end of the tapered chamber. The continuing explosive growth of the vapor bubble expels the ink from the neck 112, and causes the vapor bubble 262 and the bubble 260 to merge to form a composite bubble. The composite bubble forms about 1 ms after nucleation of the vapor bubble. The composite bubble has one surface in the tapered chamber 114 and another in the bubble capture chamber 204. Contact between the surface of the composite bubble and the walls of the tapered chamber moves the composite bubble towards the wide end of the tapered chamber. This motion draws the portion of the composite bubble located in the bubble capture chamber 204 into the primary extraction chamber 110. As a result, the part of the composite bubble occupying the bubble capture chamber shrinks, the area of the capacitative sensor 211 in contact with the ink increases, the capacitance of the capacitative sensor increases and the output of the capacitance detector 225 reverts to the first state. However, the controller 142 continues to feed current to the primary extraction heater 118.

After a predetermined time, the controller 142 discontinues the supply of current to the primary extraction heater 118 so that the heater no longer heats the composite bubble 264. The lack of heating causes the vapor component of the composite bubble to condense. The composite bubble shrinks and becomes mainly a bubble of the gas extracted from the ink. The composite bubble continues to move towards the wider end of the tapered chamber 114. During this process, the composite bubble may divide in two so that part of the composite bubble remains in the bubble capture chamber 204. The remainder of the composite bubble, or the whole composite bubble if it does not divide, finally comes to rest in part of the tapered chamber 114 remote from the neck 112.

Figure 6E:
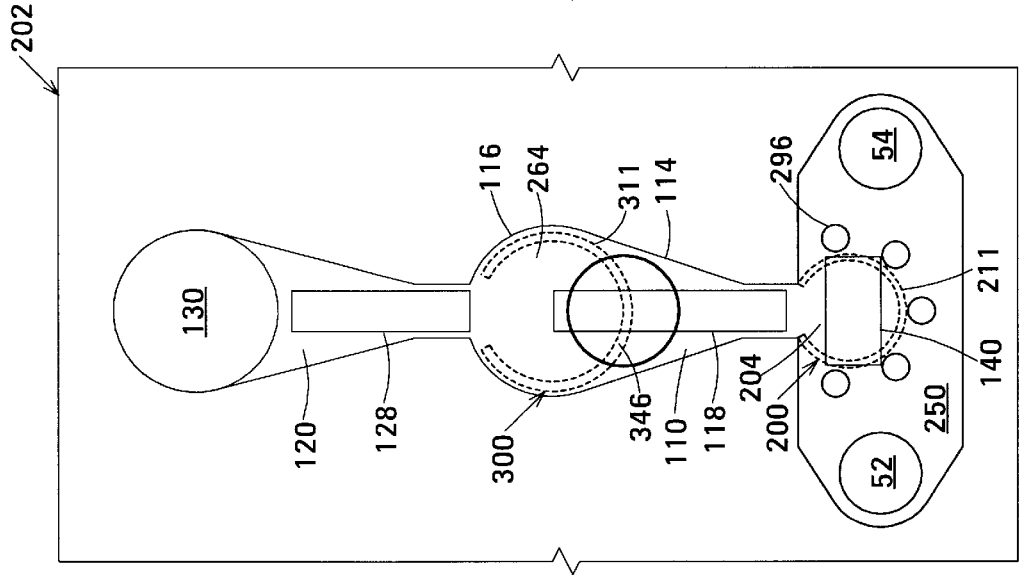
Figure 6D:
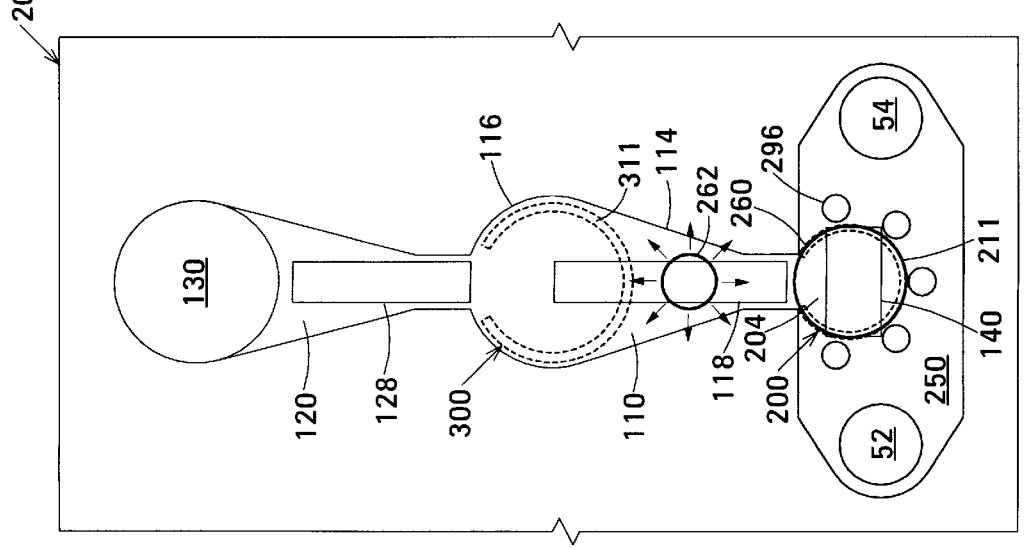

FIG. 6E shows the composite bubble 264 after it has come to rest in the tapered chamber 114. In this position, the composite bubble overlaps the portion 346 of the capacitative sensor 311 of the gas/liquid detector 300. As a result, the portion 346 of the sensor is in contact with the gas contained in the bubble. No Debye elements exist in the portion 346 of the capacitative sensor. Consequently, the capacitance of the capacitative sensor, as detected by the capacitance detector 325, is less than that detected in FIGS. 6A–6D. However, the capacitance is still relatively high because since the portion 346 is a relatively small fraction of the area of the capacitative sensor. As a result, the output of the capacitance detector remains in the first state that inhibits operation of the secondary extraction heater 128.

Additional operations of the primary extraction heater 118 in response to the gas/liquid detector 200 transfer additional gas from the bubble capture chamber 204 to the primary extraction chamber 110, increasing the size of the composite bubble 264. Another bubble of gas accumulated in the bubble capture chamber 204 is shown at 260A. As additional gas accumulates in the composite bubble 264 and the composite bubble grows, the size of the portion 346 of the capacitative sensor 311 in contact with the gas contained in the composite bubble increases. Consequently, the capacitance of the capacitative sensor 311, as detected by the capacitance detector 325, progressively falls. FIG. 6F also shows the composite bubble 264 after it has grown to a size that substantially fills the semicircular portion 116 of the tapered chamber 114. At this size, the composite bubble must be removed from the primary extraction chamber.

When the composite bubble 264 substantially fills the semicircular portion 116 of the tapered chamber 114, all or most of the capacitative sensor 311 is in contact with the gas contained in the composite bubble. Debye elements exist on little or none of the area of the capacitative sensor. Consequently, the capacitance of the capacitative sensor, as detected by the capacitance detector 325, is significantly smaller than that detected in FIGS. 6D and 6E. The capacitance detector is configured so that the capacitance of the capacitative sensor falling to the level corresponding to the composite bubble 264 covering most of the capacitative sensor 311 causes its output to change state to a second state.

In response to the change in state of the output of the capacitance detector 325, the control circuit 142 feeds current to the secondary extraction heater 128. This initiates a process similar to that described above with reference to FIG. 6D. A vapor bubble (not shown) nucleated and explosively grown by heat generated by the secondary extraction heater 128 combines with the composite bubble 264 to form a second composite bubble (not shown) with surfaces in the primary extraction chamber 110 and the secondary extraction chamber 120. The shape of the tapered chamber 124 forming part of the secondary extraction chamber moves the second composite bubble towards the exhaust manifold 130. The geometry of the secondary extraction chamber draws at least part of the second composite bubble out of the primary extraction chamber and forces at least part of the second composite bubble into the exhaust manifold.

The shrinkage of the composite bubble 264 resulting from the extraction process initiated by the secondary extraction heater 128 increases the area of the capacitative sensor 311 on which Debye elements exist, which increases the capacitance of the capacitative sensor and causes the output of the capacitance detector 325 to revert to the first state. However, the controller 142 does not stop feeding current to the secondary extraction heater until a predetermined time has elapsed.

The gas/liquid detector according to the invention can also be used in a microfluidics device to detect the pressure of the liquid relative to an ambient reference pressure. Various pressure regulators that included pressure sensors for measuring pressure difference in a microfluidics system, namely, the print head of an ink-jet printer, were disclosed in the above-mentioned U.S. patent application Ser. No. 09/116,427. The pressure sensors described in that disclosure included various forms of pressure-to-position converter that converted the ink pressure into the position of a liquid surface. The position of the liquid surface was then detected using a gas/liquid detector. The gas/liquid detectors described in the present disclosure can generate a signal that accurately indicates the fraction of the capacitative sensor that is in contact with the liquid and that can be used to indicate the position of the surface of the liquid. As an illustration of the use of the gas/liquid detectors according to the invention in a pressure regulator or pressure sensor, a version of the pressure regulator disclosed in FIG. 5I of the above-mentioned patent application that incorporates an embodiment of the gas/liquid detector according to the invention will now be described with reference to FIGS. 7A–7C. The gas/liquid detector according to the invention can easily be incorporated into the other pressure regulators and pressure sensors described in the above-mentioned patent application.

Figure 7A:
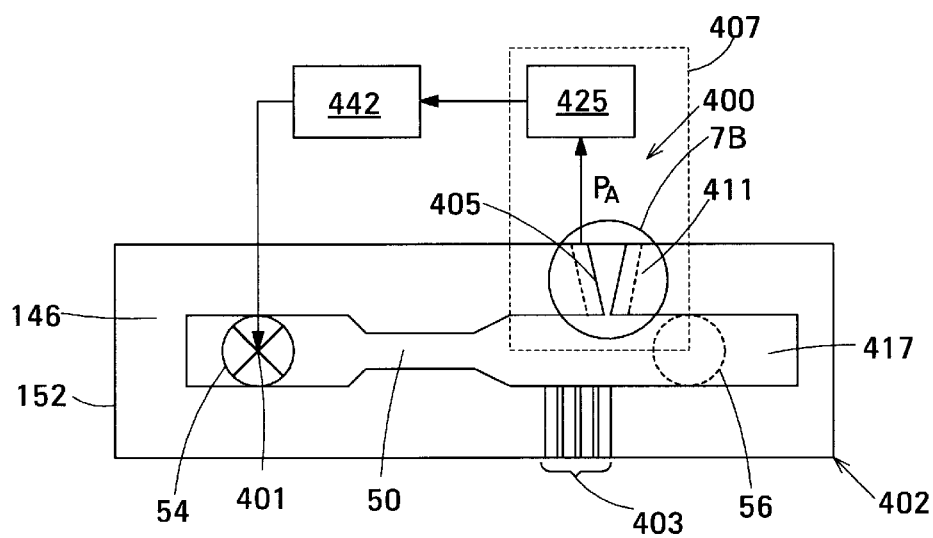
FIG. 7A is a plan view of a pressure regulator according to the invention incorporating a gas/liquid detector according to the invention. The cover of the gas extraction device has been made transparent to show the inner structure of the device.
Figure 7B:
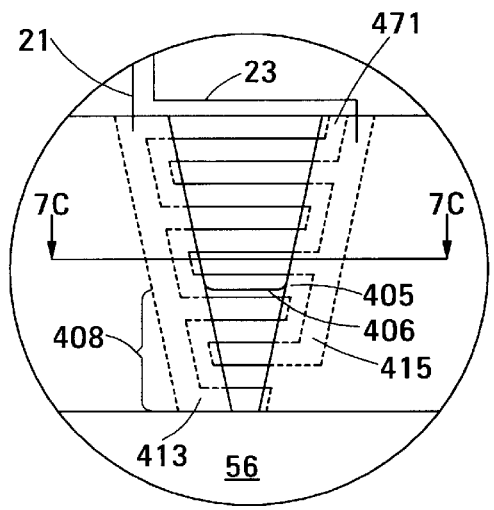
FIG. 7B is an enlarged view showing the structure and arrangement of the capacitative sensor of the gas/liquid detector in the pressure regulator shown in FIG. 7A.
Figure 7C:
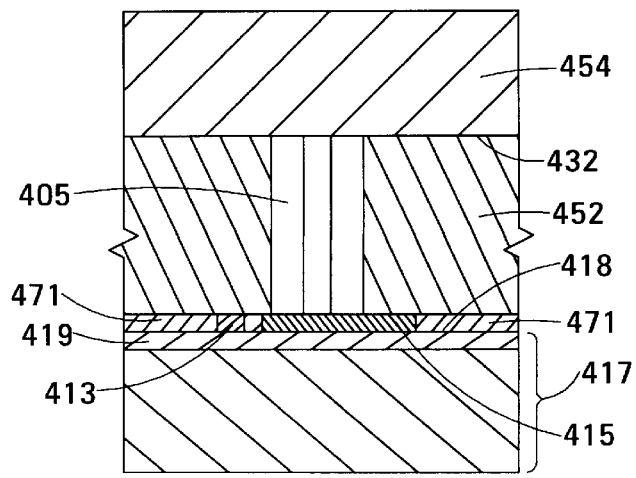
FIG. 7C is a cross-sectional view along the line 7C—7C in FIG. 7B.

In the pressure regulator 402 shown in FIGS. 7A–7C, ink flows through the ink delivery channel 50 between the ink inlet 54 and the ink outlet 56. In this embodiment, the ink inlet extends through the thickness of the substrate 417 and the ink outlet extends thought the thickness of the cover 454, but this is not critical to the invention. The pressure regulator regulates the pressure at which the ink is delivered to the ink outlet to a predetermined pressure differential below ambient pressure. The ambient pressure is typically but is not necessarily atmospheric pressure. The capillary array 403 absorbs ink from the ink delivery channel and releases ink into the ink delivery channel to regulate the ink delivery pressure to a predetermined pressure differential relative to ambient pressure. The pressure differential is determined by the geometry of the capillaries constituting the array and by the wetting properties of the ink with respect to the material from which the capillary array is fabricated.

However, since the ink capacity of the capillary array 403 is limited, the pressure regulator includes a second pressure regulator composed of the valve 401 that operates in response to the controller 442. The controller operates in response to the pressure sensor 407. The pressure sensor is composed of the tapered capillary 405 and the liquid/gas detector 400 according to the invention. The liquid/gas detector is composed of the capacitative sensor 411 and the capacitance detector 425.

The tapered capillary 405 acts as the pressure-to-position converter in this embodiment. The position of the ink surface (406 in FIG. 7B) depends on the difference between the ink pressure and the ambient pressure $P_A$. The capacitance of the capacitative sensor 411 depends on the position of the ink surface in the tapered capillary.

The tapered capillary 405 extends laterally from the ink delivery channel 50 to a point in pressure communication with the ambient pressure $P_A$. The side walls of the tapered capillary are tapered so that the capillary increases in width with increasing distance from the ink delivery channel. The top wall of the tapered capillary is provided by the surface 432 of the cover 454. The bottom wall of the tapered capillary is provided partially by the electrodes 413 and 415 and partially by the planarizing layer 471. The planarizing layer may be omitted if not required. The level of the ink surface 406 in the tapered capillary 405 depends on the pressure differential between the ambient pressure $P_A$ and the pressure in the ink delivery channel. The level of the ink surface in the tapered capillary is detected by the gas/liquid detector 400 located on the bottom wall of the tapered capillary.

The pressure regulator 402 is constructed on the substrate 417 using conventional micromachining techniques. The substrate is part of a wafer of silicon or some other suitable semiconducting or insulating material. The substrate is shown as including the insulating layer 419 on which the electrodes constituting the capacitative sensor 411 are located, although this layer can be omitted if the substrate is fabricated from an insulating material. The insulating layer 419, if required, may be a layer of silicon dioxide, silicon nitride or other suitable insulator grown or deposited on the surface of the wafer.

The capacitance detector 425 is preferably formed near the capacitative sensor 411 on and under the surface 118 of the substrate, although this is not critical to the invention. The capacitative sensor including the electrodes 413 and 415, and including the planarizing layer 471 when necessary, is formed on the surface of the substrate using any of the ways described above. The electrodes 413 and 415 are comb-shaped and are interleaved with one another so that adjacent fingers of the electrodes preferably extend substantially parallel to one another.

A layer of barrier material 452 is then deposited on the surface of the wafer, covering the capacitative sensor 411. Then, the ink delivery channel 50, the capillary array 403 and the tapered capillary 405 are formed by selectively removing parts of the barrier material. Forming the tapered capillary exposes the capacitative sensor. The wafer is then fitted with the cover 454 and is divided into individual pressure regulators.

The capacitance detector 425 is configured to apply an alternating voltage between the electrodes 413 and 415 having an amplitude that is less, by a suitable safety margin, than the voltage at which the Debye elements that exist on the portions of the electrodes in contact with the ink cease to be predominantly capacitative.

FIG. 7B shows the ink surface 406 in the tapered capillary 405. With the ink surface positioned as shown, the portion 408 of the capacitative sensor 411 is immersed in ink, and Debye elements exist on the portions of the electrodes 413 and 415 in contact with the ink. The remainder of the capacitative sensor is in contact with air, and therefore contributes little to the capacitance measured by the capacitance detector 425. Accordingly, the capacitance measured by the capacitance detector depends on the fraction of the area of the capacitance detector that is in contact with the ink, the capacitance increasing as the ink level rises in the tapered capillary.

The ink level rises in the tapered capillary 405 in response to the pressure in the ink delivery channel 50 increasing towards ambient pressure. Since the pressure in the ink delivery channel should be maintained below ambient pressure, an increase in the capacitance measured by the capacitance detector 425 indicates that the valve 401 should be closed to prevent the ink pressure rising further. Accordingly, the capacitance detector is configured to generate an output signal that changes state when the capacitance measured by the capacitance detector increases above a first predetermined level, and to revert back to its original state when the capacitance falls below a second predetermined level. The predetermined levels can be the same, but the first predetermined level is preferably greater than the second to provide hysteresis. The controller 442 operates in response to the output signal generated by the capacitance detector to close and open the valve 401. The capacitance detector and controller may be embodied in a common physical circuit.

In a practical pressure regulator, the number of fingers on each of the electrodes 413 and 415 is substantially greater than the number shown in FIG. 7B to reduce quantizing effects. Moreover, the fingers of the electrodes can extend along the length of the tapered capillary 405, instead of extending perpendicular to the length as shown.

As an alternative to the tapered capillary 405, the capacitative sensor 411 can underlay an array of non-tapered capillaries of different sizes. As the pressure in the ink delivery channel changes, the number of capillaries in the array that are full of ink will also change. Debye elements exist only on the parts of the electrodes of the capacitative sensor that underlie the capillaries that are full of ink and are absent from the parts of the electrodes that underlie the capillaries that are empty. As a result, the capacitance of the capacitative sensor depends on the number of capillaries that are full of ink and, hence, on the difference between the pressure in the ink delivery channel and ambient pressure.

In the embodiments of the gas/liquid detector according to the invention described above, the electrodes constituting the capacitative sensor extend substantially parallel to one another on a surface, as in the embodiment shown in FIGS. 1A and 1B, or are concentric with one another, as in the embodiment shown in FIGS. 4A–4D. It is also noted above that the electrodes could alternatively be located opposite one another on two opposed substrates. Moreover, in the embodiments described above, both electrodes constituting the sensor are of similar area and are substantially simultaneously in contact, or not in contact, with the liquid. However, the electrodes being disposed parallel to one another, opposite one another or concentric with one another, the electrodes being similar in area, and the electrodes being substantially simultaneously in contact or not in contact with the liquid are not critical to the invention.

In embodiments in which the portion of the liquid that extends between one of the electrodes constituting the capacitative sensor and the other has a resistance that is sufficiently low that the serial arrangement of the Debye elements and the liquid is substantially capacitative, the electrodes can be separated from one another, need not be aligned parallel to, opposite or concentric with one another, need not be similar in area, and need not simultaneously be in contact or not in contact with the liquid. Not having to comply with such constraints enables the structures of the electrodes and of the capacitative sensor incorporating the electrodes to be simplified. For example, the electrodes can have simpler shapes, and, since the electrodes need not have a comb structure, the need to planarize the surface that the sensor presents to the liquid does not arise. Moreover, one of the electrodes can be made substantially larger than the other, and can be located in a position where it is always in contact with the liquid. Increasing the size of the one of the electrodes increases the capacitance change that occurs when the sensor comes into contact with the liquid. This is because the capacitance of two capacitors in series is greater when one of the capacitors has a greater capacitance than the other than when the capacitors have approximately equal capacitances. Finally, the electrodes can more easily be fabricated from two different materials.

FIGS. 8A–8C show an example of an embodiment 500 of the gas/liquid detector according to the invention in which the electrodes constituting the capacitative sensor are not parallel to, opposite or concentric with one another and in which the Debye element adjacent one of the electrodes has a substantially greater capacitance than the Debye element adjacent the other. Also in the embodiment shown in FIGS. 8A–8C, one of the electrodes is in permanent contact with the liquid, and the output signal of the capacitance detector depends on the state of contact between the other of the electrodes and the liquid or the fraction of the area of the other of the electrodes that is in contact with the liquid. The gas/liquid detector will be described with reference to an example in which the gas/liquid detector is used to determine the size of the bubble accumulated in the bubble capture chamber of the gas extraction device 502. This gas extraction device is similar to the gas extraction device 402 described above with reference to FIGS. 4A–4D. Elements of the gas extraction device and of the gas/liquid detector shown in FIGS. 8A–8C that correspond to elements of the gas extraction device and of the gas/liquid detector shown in FIGS. 4A–4D are indicated using the same reference numerals and will not be described again here.

FIGS. 8A–8C show the gas/liquid detector 500 installed in the gas extraction device 502. The structure and construction of the gas extraction device 502 is the same as that of the gas extraction device 202 shown in FIGS. 4A–4C, and will not be described again. The liquid/gas detector is composed of the capacitative sensor 511 and the capacitance detector 525. The capacitative sensor is composed of the electrodes 513 and 515. The electrode 513 is located on the part of the surface 132 of the cover 154 that provides the ceiling of the bubble capture chamber 204. The capacitance detector 525 is preferably formed in and on the surface 132 of the cover, adjacent the electrode 513, although this is not critical to the invention. The electrode 513 is composed of a single conductive member that is curved to follow the periphery of the bubble capture chamber 204 defined by the pillars including the exemplary pillars 292 and 293. The electrode may optionally be slightly inset from the periphery. The simpler structure of the electrode 513 compared with that of the comb-shaped electrodes 213 and 215 can be seen by comparing FIG. 8C with FIG. 4D. The electrode 513 lacks the recesses that exist between adjacent fingers of the interleaved electrodes 213 and 215 and therefore requires no planarizing. Thus, fabrication of the electrode 513 is simpler than fabrication of the electrodes 213 and 215.

The electrode 515 is supported by the surface 150 of the substrate 102 and covers most of the surface 150 exposed at the bottom of the ink delivery channel 250 outside the bubble capture chamber 204. The simple shape and large feature sizes of the electrode 515 simplify fabrication. The electrode is in constant contact with the ink flowing through the ink delivery channel, and its area is several times larger than the area of the electrode 513.

The electrodes 513 and 515 are connected to the capacitance detector 525 by suitable conductors. The circuit shown in FIG. 3 may be used as the capacitance detector, for example. The capacitance detector is configured to apply an alternating voltage between the electrodes 513 and 515 having an amplitude that is less, by a suitable safety margin, than the voltage at which the Debye elements that exist on the electrodes when the ink contacts the electrodes cease to be predominantly capacitive.

During normal operation of the printer in which the gas extraction device 502 is installed, the electrode 515 is in constant contact with the ink, and a large-area Debye element constantly exists on the surface of this electrode. The large-area Debye element has an area substantially equal to the area of the ink delivery channel 250 outside the bubble capture chamber 204. In addition, a smaller Debye element covers the portion of the area of the electrode 513 that is in contact with the ink. The size of this Debye element depends on the size of the gas bubble that has accumulated in the bubble capture chamber. The Debye elements are electrically connected in series by conduction through the ink, as described above. The capacitance detector 525 connected to the electrodes 513 and 515 measures the capacitance between the electrodes. The measured capacitance is substantially equal to that of the Debye element that exists on the part of the surface of the electrode 513 in contact with the ink since the capacitance of this Debye element is small compared with that of the Debye element that exists on the surface of the electrode 515. Thus, the capacitance detector can easily detect the capacitance changes that indicate the size of the bubble that accumulates in the bubble capture chamber.

The electrical arrangement of the gas extraction device 502 is the same as that of the gas extraction device 202 shown in FIG. 5, and will not be described again here. Fabrication and operation of the gas extraction device 502 are the same as those of the gas extraction device 202 described above with reference to FIGS. 4A–4C and FIGS. 6A–6F, and so will not be described again here.

The locations of the electrodes 513 and 515 constituting the sensor 511 are not critical to the invention as long as they are located so that the ink can provide a conduction path of a sufficiently low impedance between them. The smaller of the electrodes, the electrode 513, should be sited at the location where it is desired to detect the presence or absence of the ink. For example, the electrode can alternatively detect the size of the bubble in the bubble capture chamber 204 if the size of the gas release heater 140 is reduced, and the electrode 513 is relocated to the surface 150 of the substrate 102. Additionally or alternatively, the electrode 515 can be moved to the surface 132 of the cover 154, and its size optionally can be increased to overlap either or both of the ink inlet 52 and the ink inlet 54. As a further alternative, the size of the electrode 515 can be reduced so that the electrode occupies only part of the ink delivery channel outside the bubble capture chamber.

As noted above, the electrodes 513 and 515 may be made of different materials. In particular, the electrode 515 can be made of a low work-function metal such as gold or platinum whereas the electrode 513 can be made of an oxidizing metal such as a tantalum-aluminum alloy. When the electrode 515 is made of a low work-function metal, the conductance of the shunt conductor in the Debye element that exists on this electrode is so high that the Debye element is predominantly conductive, and the electrode 515 provides a substantially ohmic contact with the ink. In this case, only the Debye element that exists on the electrode 513 when the electrode is in contact with the ink has a measurable capacitance. The electrode 513 provides a direct electrical connection to one plate of the Debye capacitor in the Debye element that exists on this electrode, and the electrode 515 provides an ohmic connection to the other plate of the Debye capacitor through the liquid. The measured capacitance of the Debye capacitor that exists on the electrode 513 may be somewhat higher than that measured when the electrode 515 is made of tantalum or other oxidizing metal. This is because, when the electrode 515 makes an ohmic contact with the liquid, the measured capacitance of the Debye element that exists on the electrode 513 is not reduced by the series capacitance of the Debye capacitor that exists on the electrode 515.

Although this disclosure describes illustrative embodiments of the invention in detail, it is to be understood that the invention is not limited to the precise embodiments described, and that various modifications may be practiced within the scope of the invention defined by the appended claims. In particular, the applications of the gas/liquid detector are not limited to those described. For example, the gas/liquid detector could be applied to other embodiments of the pressure regulator described in the above-mentioned patent application Ser. No. 09/116,427. Moreover, the gas/liquid detector could also be used to monitor the locations and sizes of the bubbles in the bubble valves described in the above-mentioned patent application Ser. No. 09/114,978.

We claim:

1. A detector for an ionic liquid, the detector comprising:
   a capacitative sensor having a capacitance and including a pair of electrodes separated from one another, the electrodes being positioned to be capable of contact with the ionic liquid, contact between a one of the electrodes and the ionic liquid forming a Debye element in the ionic liquid, the Debye element including a capacitative element and an associated shunt conductor, the shunt conductor having an exponentially-increasing conductance-versus-voltage characteristic; and
   a capacitance detector connected to the capacitative sensor and measuring the capacitance thereof by applying an alternating voltage between the electrodes, the alternating voltage having a voltage amplitude less than a voltage amplitude at which the Debye element ceases to be predominantly capacitative.

2. The detector of claim 1, in which:
each of electrodes includes:
an interconnecting element, and
elongate fingers extending from the interconnecting element; and
the elongate fingers of one of the electrodes are interleaved with the elongate fingers of the other of the electrodes.

3. The detector of claim 1, in which:
the capacitative sensor additionally includes a substrate of a semiconductor material; and
each of the electrodes includes a region of a high concentration of an impurity introduced into the substrate.

4. The detector of claim 1, in which:
the capacitative sensor additionally comprises:
a substrate having an insulating region adjacent a major surface of the substrate, and
a planarizing layer supported by the major surface of the substrate;
each of the electrodes comprises a layer of metal supported by the major surface of the substrate; and
the planarizing layer at least partly fills a recess defined by the electrodes and the major surface of the substrate.

5. The detector of claim 1, in which the capacitance detector generates an output signal in a first state when the capacitance of the capacitative sensor is greater than a first threshold and generates the output signal in a second state when the capacitance of the capacitative sensor is less than a second threshold.

6. The detector of claim 1, in which:
the one of the electrodes is positioned at a location where contact between the liquid and the electrode varies; and
the other of the electrodes is positioned at a location in permanent contact with the liquid.

7. The detector of claim 6, in which the other of the electrodes has a greater area than the one of the electrodes.

8. The detector of claim 6, in which the other of the electrodes is fabricated from a material having a low work function and forms a substantially ohmic contact with the liquid.

9. The detector of claim 1, in which at least one of the electrodes is fabricated from an oxidizing metal.

10. The detector of claim 9, in which the at least one of the electrodes includes an element selected a group consisting of tantalum and aluminum.

11. A gas extraction device for removing gas from an ionic liquid, the gas extraction device comprising:
a bubble capture chamber structured to accumulate a bubble of gas, the bubble chamber having a perimeter;
the detector of claim 1, in which:
at least one of the electrodes constituting the capacitative sensor is located in the bubble capture chamber and is shaped to substantially follow the perimeter of the bubble capture chamber, and
the capacitance detector generates an output signal that changes state when the bubble of gas accumulated in the bubble capture chamber has grown to a predetermined size and overlaps at least part of the capacitative sensor; and
a bubble removal system coupled to the bubble capture chamber and operating in response to the output signal of the capacitance detector to extract the bubble of gas from the bubble capture chamber.

12. The gas extraction device of claim 11, in which:
the detector is a first detector and includes a first capacitative sensor and a first capacitance detector;
the bubble removal system is a first bubble removal system;
the first bubble removal system includes a primary extraction chamber including a tapered chamber comprising a substantially semicircular portion; and
the gas extraction device additionally comprises a second detector of claim 1, the second detector including a second capacitative sensor and a second capacitance detector, in which:
at least one of the electrodes of the second capacitative sensor is located in the semicircular portion of the tapered chamber, and
the second capacitance detector generates an output signal that changes state when the bubble of gas accumulated in the tapered chamber has grown to a predetermined size and overlaps at least part of the second capacitative sensor; and
the gas extraction device additionally comprises a second bubble removal system coupled to the primary extraction chamber and operating in response to the output signal of the second capacitance detector to remove the bubble from the primary extraction chamber.

13. A pressure sensor for determining the pressure of an ionic liquid, the pressure sensor comprising:
a pressure-to-position converter in pressure communication with the liquid and configured to establish a liquid surface whose position depends on the pressure of the liquid; and
the detector of claim 1, in which:
the one of the electrodes of the capacitative sensor is located to contact the liquid in the pressure-to-position converter, and
a fraction of the area of the one of the electrodes of the capacitative sensor that is in contact with the liquid depends on the position of the liquid surface.

14. The pressure sensor of claim 13, in which:
the pressure-to-position converter includes a capillary having a length, and a cross-sectional area that varies along the length; and
the one of the electrodes of the capacitative sensor is located to contact the liquid along the length of the capillary.

15. The pressure sensor of claim 13, in which:
the pressure-to-position converter comprises an array of capillaries of different cross-sectional areas; and
the one of the electrodes of the capacitative sensor is located to contact the liquid along the lengths of the capillaries.

16. A detector for an ionic liquid, the detector comprising:
a capacitative sensor having a capacitance and including:
a first electrode and a second electrode separated from one another, and
Debye elements extant in the liquid adjacent such portions of the electrodes that are in contact with the liquid, the Debye elements each including a Debye capacitor with an associated shunt conductor, the shunt conductor having an exponentially-increasing conductance versus voltage characteristic, the Debye element adjacent the first electrode and the Debye element adjacent the second electrode being connected in series by the liquid, the Debye element adjacent at least the first electrode having a substantially greater capacitance than a capacitance between the electrodes absent the Debye elements; and
a capacitance detector connected to the capacitative sensor and measuring the capacitance thereof by applying an alternating voltage between the electrodes, the alternating voltage having a voltage amplitude less than a voltage amplitude at which the Debye element extant adjacent at least the first electrode ceases to be predominantly capacitative.

17. The detector of claim 16, in which:
the first electrode and the second electrode each include:
an interconnecting element, and
elongate fingers extending from the interconnecting element; and
the elongate fingers of the first electrode are interleaved with the elongate fingers of the second electrode.

18. The detector of claim 16, in which:
the capacitative sensor additionally includes a substrate of a semiconductor material; and
the first electrode and the second electrode each include a region of the substrate comprising a high concentration of an impurity.

19. The detector of claim 16, in which:
the first electrode is positioned at a location where contact between the liquid and the electrode varies; and
the second electrode is positioned at a location in permanent contact with the liquid.

20. The detector of claim 19, in which the second electrode has a greater area than the first electrode.

21. The detector of claim 19, in which the second electrode is fabricated from a material having a low work function and forms a substantially ohmic contact with the liquid.

22. The detector of claim 16, in which at least one of the first electrode and the second electrode is fabricated from an oxidizing metal.

23. The detector of claim 22, in which the at least one of the first electrode and the second electrode includes an element selected a group consisting of tantalum and aluminum.

* * * * *